(12) United States Patent
Dumbauld et al.

(10) Patent No.: US 7,846,161 B2
(45) Date of Patent: Dec. 7, 2010

(54) INSULATING BOOT FOR ELECTROSURGICAL FORCEPS

(75) Inventors: Patrick L. Dumbauld, Lyons, CO (US); Paul Guerra, Boulder, CO (US); Roger F. Smith, Boulder, CO (US); Scott DePierro, Madison, CT (US)

(73) Assignee: Covidien AG, Neuhausen am Rheinfall (CH)

( * ) Notice: Subject to any disclaimer, the term of this patent is extended or adjusted under 35 U.S.C. 154(b) by 780 days.

(21) Appl. No.: 11/529,798

(22) Filed: Sep. 29, 2006

(65) Prior Publication Data

US 2007/0078458 A1 Apr. 5, 2007

Related U.S. Application Data

(60) Provisional application No. 60/722,213, filed on Sep. 30, 2005, provisional application No. 60/722,186, filed on Sep. 30, 2005, provisional application No. 60/722,359, filed on Sep. 30, 2005.

(51) Int. Cl.
*A61B 18/18* (2006.01)
(52) U.S. Cl. .............................. 606/51; 606/45; 606/52
(58) Field of Classification Search .............. 606/50–52
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,279,753 A | 4/1942 | Knopp |
| 2,305,156 A | 12/1942 | Grubel |
| 2,327,353 A | 8/1943 | Karle |

(Continued)

FOREIGN PATENT DOCUMENTS

CA         2104423         2/1994

(Continued)

OTHER PUBLICATIONS

Int'l Search Report EP 05016399 dated Jan. 5, 2006.

(Continued)

*Primary Examiner*—Thomas J Sweet
*Assistant Examiner*—Amanda Scott

(57) ABSTRACT

Either an endoscopic or open bipolar forceps includes a flexible, generally tubular insulating boot for insulating patient tissue, while not impeding motion of the jaw members. The jaw members are movable from an open to a closed position and the jaw members are connected to a source of electrosurgical energy such that the jaw members are capable of conducting energy through tissue held therebetween to effect a tissue seal. A knife assembly may be included that allows a user to selectively divide tissue upon actuation thereof. The insulating boot may be made from a viscoelastic, elastomeric or flexible material suitable for use with a sterilization process including ethylene oxide.

8 Claims, 28 Drawing Sheets

U.S. PATENT DOCUMENTS

| | | | |
|---|---|---|---|
| 2,632,661 A | 3/1953 | Cristofv | |
| 2,668,538 A | 2/1954 | Baker | |
| 2,796,065 A | 6/1957 | Kapp | |
| 3,073,311 A | 1/1963 | Tibbs et al. | |
| 3,372,288 A | 3/1968 | Wigington | |
| 3,459,187 A | 8/1969 | Pallotta | |
| 3,643,663 A | 2/1972 | Sutter | |
| 3,648,001 A | 3/1972 | Anderson et al. | |
| 3,651,811 A | 3/1972 | Hildebrandt et al. | |
| 3,678,229 A | 7/1972 | Osika | |
| 3,720,896 A | 3/1973 | Beierlein | |
| 3,763,726 A | 10/1973 | Hildebrand | |
| 3,779,918 A | 12/1973 | Ikeda et al. | |
| 3,801,766 A | 4/1974 | Morrison, Jr. | |
| 3,862,630 A | 1/1975 | Balamuth | |
| 3,863,339 A | 2/1975 | Reaney et al. | |
| 3,866,610 A | 2/1975 | Kletschka | |
| 3,897,786 A * | 8/1975 | Garnett et al. | 606/109 |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,016,881 A | 4/1977 | Rioux et al. | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,076,028 A | 2/1978 | Simmons | |
| 4,080,820 A | 3/1978 | Allen | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,187,420 A | 2/1980 | Piber | |
| 4,233,734 A | 11/1980 | Bies | |
| 4,236,470 A | 12/1980 | Stenson | |
| 4,300,564 A | 11/1981 | Furihata | |
| 4,311,145 A | 1/1982 | Esty et al. | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,443,935 A | 4/1984 | Zamba et al. | |
| 4,452,246 A | 6/1984 | Bader et al. | |
| 4,470,786 A | 9/1984 | Sano et al. | |
| 4,492,231 A | 1/1985 | Auth | |
| 4,493,320 A | 1/1985 | Treat | |
| 4,503,855 A | 3/1985 | Maslanka | |
| 4,506,669 A | 3/1985 | Blake, III | |
| 4,509,518 A | 4/1985 | McGarry et al. | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,624,254 A | 11/1986 | McGarry et al. | |
| 4,655,215 A | 4/1987 | Pike | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| 4,733,662 A | 3/1988 | DeSatnick et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,829,313 A | 5/1989 | Taggart | |
| 4,846,171 A | 7/1989 | Kauphusman et al. | |
| 4,887,612 A | 12/1989 | Esser et al. | |
| 4,938,761 A | 7/1990 | Ensslin | |
| 4,947,009 A | 8/1990 | Osika et al. | |
| 4,985,030 A | 1/1991 | Melzer et al. | |
| 5,007,908 A | 4/1991 | Rydell | |
| 5,026,370 A | 6/1991 | Lottick | |
| 5,026,371 A | 6/1991 | Rydell et al. | |
| 5,035,695 A | 7/1991 | Weber, Jr. et al. | |
| 5,037,433 A | 8/1991 | Wilk et al. | |
| 5,042,707 A | 8/1991 | Taheri | |
| 5,047,046 A | 9/1991 | Bodoia | |
| 5,078,716 A | 1/1992 | Doll | |
| 5,084,057 A | 1/1992 | Green et al. | |
| 5,085,659 A | 2/1992 | Rydell | |
| 5,099,840 A | 3/1992 | Goble et al. | |
| 5,100,430 A | 3/1992 | Avellanet et al. | |
| 5,108,392 A | 4/1992 | Spingler | |
| 5,112,343 A | 5/1992 | Thornton | |
| 5,116,332 A | 5/1992 | Lottick | |
| 5,147,357 A | 9/1992 | Rose et al. | |
| 5,151,102 A | 9/1992 | Xamiyama et al. | |
| 5,151,978 A | 9/1992 | Bronikowski et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,209,747 A | 5/1993 | Knoepfler | |
| 5,211,655 A | 5/1993 | Hasson | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,282,800 A | 2/1994 | Foshee et al. | |
| 5,282,826 A | 2/1994 | Quadri | |
| 5,290,286 A | 3/1994 | Parins | |
| 5,300,082 A | 4/1994 | Sharpe et al. | |
| 5,304,203 A | 4/1994 | El-Mallawany et al. | |
| 5,308,353 A | 5/1994 | Beurrier | |
| 5,308,357 A | 5/1994 | Lichtman | |
| 5,313,027 A | 5/1994 | Inoue et al. | |
| 5,314,445 A | 5/1994 | Degwitz et al. | |
| 5,318,589 A | 6/1994 | Lichtman | |
| 5,324,289 A | 6/1994 | Eggers | |
| D348,930 S | 7/1994 | Olson | |
| 5,326,806 A | 7/1994 | Yokoshima et al. | |
| 5,330,471 A | 7/1994 | Eggers | |
| 5,330,502 A | 7/1994 | Hassler et al. | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,350,391 A | 9/1994 | Iacovelli | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |

| | | | | | |
|---|---|---|---|---|---|
| 5,367,250 A * | 11/1994 | Whisenand ............... 324/133 | 5,564,615 A | 10/1996 | Bishop et al. |
| 5,368,600 A | 11/1994 | Failla et al. | 5,569,241 A | 10/1996 | Edwardds |
| 5,374,277 A | 12/1994 | Hassler | 5,569,243 A | 10/1996 | Kortenbach et al. |
| 5,376,089 A | 12/1994 | Smith | 5,571,100 A | 11/1996 | Goble et al. |
| 5,383,875 A | 1/1995 | Bays et al. | 5,573,424 A | 11/1996 | Poppe |
| 5,383,897 A | 1/1995 | Wholey | 5,573,534 A | 11/1996 | Stone |
| 5,389,098 A | 2/1995 | Tsuruta et al. | 5,573,535 A | 11/1996 | Viklund |
| 5,389,103 A | 2/1995 | Melzer et al. | 5,575,799 A | 11/1996 | Bolanos et al. |
| 5,389,104 A | 2/1995 | Hahnen et al. | 5,575,805 A | 11/1996 | Li |
| 5,391,166 A | 2/1995 | Eggers | 5,578,052 A | 11/1996 | Koros et al. |
| 5,391,183 A | 2/1995 | Janzen et al. | 5,579,781 A | 12/1996 | Cooke |
| 5,396,900 A | 3/1995 | Slater et al. | 5,582,611 A | 12/1996 | Tsukagoshi et al. |
| 5,403,312 A | 4/1995 | Yates et al. | 5,582,617 A | 12/1996 | Klieman et al. |
| 5,403,342 A | 4/1995 | Tovey et al. | 5,585,896 A | 12/1996 | Yamazaki et al. |
| 5,405,344 A | 4/1995 | Williamson et al. | 5,590,570 A | 1/1997 | LeMaire, III et al. |
| 5,409,763 A | 4/1995 | Serizawa et al. | 5,591,181 A | 1/1997 | Stone et al. |
| 5,411,519 A | 5/1995 | Tovey et al. | 5,597,107 A | 1/1997 | Knodel et al. |
| 5,411,520 A | 5/1995 | Nash et al. | 5,601,224 A | 2/1997 | Bishop et al. |
| 5,413,571 A | 5/1995 | Katsaros et al. | 5,601,601 A | 2/1997 | Tal et al. |
| 5,415,656 A | 5/1995 | Tihon et al. | 5,601,641 A | 2/1997 | Stephens |
| 5,415,657 A | 5/1995 | Taymor-Luria | 5,603,711 A | 2/1997 | Parins et al. |
| 5,422,567 A | 6/1995 | Matsunaga | 5,603,723 A | 2/1997 | Aranyi et al. |
| 5,423,810 A | 6/1995 | Goble et al. | 5,611,798 A | 3/1997 | Eggers |
| 5,425,690 A | 6/1995 | Chang | 5,611,808 A | 3/1997 | Hossain et al. |
| 5,425,739 A | 6/1995 | Jessen | 5,611,813 A | 3/1997 | Lichtman |
| 5,429,616 A | 7/1995 | Schaffer | 5,620,415 A | 4/1997 | Lucey et al. |
| 5,431,672 A | 7/1995 | Cote et al. | 5,620,453 A | 4/1997 | Nallakrishnan |
| 5,431,674 A | 7/1995 | Basile et al. | 5,620,459 A | 4/1997 | Lichtman |
| 5,437,292 A | 8/1995 | Kipshidze et al. | 5,624,452 A | 4/1997 | Yates |
| 5,438,302 A | 8/1995 | Goble | 5,626,578 A | 5/1997 | Tihon |
| 5,439,478 A | 8/1995 | Palmer | 5,626,609 A | 5/1997 | Zvenyatsky et al. |
| 5,441,517 A | 8/1995 | Kensey et al. | 5,630,833 A | 5/1997 | Katsaros et al. |
| 5,443,463 A | 8/1995 | Stern et al. | 5,637,110 A | 6/1997 | Pennybacker et al. |
| 5,443,464 A | 8/1995 | Russell et al. | 5,638,003 A | 6/1997 | Hall |
| 5,443,480 A | 8/1995 | Jacobs et al. | 5,643,294 A | 7/1997 | Tovey et al. |
| 5,445,638 A | 8/1995 | Rydell et al. | 5,647,869 A | 7/1997 | Goble et al. |
| 5,445,658 A | 8/1995 | Durrfeld et al. | 5,647,871 A | 7/1997 | Levine et al. |
| 5,449,480 A | 9/1995 | Kuriya et al. | 5,649,959 A | 7/1997 | Hannam et al. |
| 5,451,224 A | 9/1995 | Goble et al. | 5,655,650 A | 8/1997 | Naitou |
| 5,454,823 A | 10/1995 | Richardson et al. | 5,658,281 A | 8/1997 | Heard |
| 5,454,827 A | 10/1995 | Aust et al. | D384,413 S | 9/1997 | Zlock et al. |
| 5,456,684 A | 10/1995 | Schmidt et al. | 5,662,667 A | 9/1997 | Knodel |
| 5,458,598 A | 10/1995 | Feinberg et al. | 5,665,100 A | 9/1997 | Yoon |
| 5,460,629 A | 10/1995 | Shlain et al. | 5,667,526 A | 9/1997 | Levin |
| 5,461,765 A | 10/1995 | Linden et al. | 5,674,220 A | 10/1997 | Fox et al. |
| 5,462,546 A | 10/1995 | Rydell | 5,674,229 A | 10/1997 | Tovey et al. |
| 5,472,442 A | 12/1995 | Klicek | 5,681,282 A | 10/1997 | Eggers et al. |
| 5,472,443 A | 12/1995 | Cordis et al. | 5,688,270 A | 11/1997 | Yates et al. |
| 5,478,351 A | 12/1995 | Meade et al. | 5,690,652 A | 11/1997 | Wurster et al. |
| 5,480,406 A | 1/1996 | Nolan et al. | 5,690,653 A | 11/1997 | Richardson et al. |
| 5,480,409 A | 1/1996 | Riza | 5,693,051 A | 12/1997 | Schulze et al. |
| 5,484,436 A | 1/1996 | Eggers et al. | 5,693,920 A | 12/1997 | Maeda |
| 5,496,312 A | 3/1996 | Klicek | 5,695,522 A | 12/1997 | LeMaire, III et al. |
| 5,496,317 A | 3/1996 | Goble et al. | 5,700,261 A | 12/1997 | Brinkerhoff |
| 5,496,347 A | 3/1996 | Hashiguchi et al. | 5,700,270 A | 12/1997 | Peyser et al. |
| 5,499,997 A | 3/1996 | Sharpe et al. | 5,702,390 A | 12/1997 | Austin et al. |
| 5,509,922 A | 4/1996 | Aranyi et al. | 5,707,369 A | 1/1998 | Vaitekunas et al. |
| 5,514,134 A | 5/1996 | Rydell et al. | 5,709,680 A | 1/1998 | Yates et al. |
| 5,527,313 A | 6/1996 | Scott et al. | 5,716,366 A | 2/1998 | Yates |
| 5,528,833 A | 6/1996 | Sakuma | 5,720,744 A | 2/1998 | Eggleston et al. |
| 5,529,067 A | 6/1996 | Larsen et al. | 5,722,421 A | 3/1998 | Francese et al. |
| 5,531,744 A | 7/1996 | Nardella et al. | 5,725,536 A | 3/1998 | Oberlin et al. |
| 5,536,251 A | 7/1996 | Evard et al. | 5,727,428 A | 3/1998 | LeMaire, III et al. |
| 5,540,684 A | 7/1996 | Hassler, Jr. | 5,735,848 A | 4/1998 | Yates et al. |
| 5,540,685 A | 7/1996 | Parins et al. | 5,743,906 A | 4/1998 | Parins et al. |
| 5,540,706 A | 7/1996 | Aust et al. | 5,752,973 A | 5/1998 | Kieturakis |
| 5,540,715 A | 7/1996 | Katsaros et al. | 5,755,717 A | 5/1998 | Yates et al. |
| 5,542,945 A | 8/1996 | Fritzsch | 5,759,188 A | 6/1998 | Yoon |
| 5,558,671 A | 9/1996 | Yates | 5,766,130 A | 6/1998 | Selmonosky |
| 5,558,672 A | 9/1996 | Edwards et al. | 5,766,166 A | 6/1998 | Hooven |
| 5,562,619 A | 10/1996 | Mirarchi et al. | 5,766,170 A | 6/1998 | Eggers |
| 5,562,699 A | 10/1996 | Heimberger et al. | 5,766,196 A | 6/1998 | Griffiths |
| 5,562,720 A | 10/1996 | Stern et al. | 5,769,849 A | 6/1998 | Eggers |

| | | | | | |
|---|---|---|---|---|---|
| 5,772,655 A | 6/1998 | Bauer et al. | 5,984,938 A | 11/1999 | Yoon |
| 5,772,670 A | 6/1998 | Brosa | 5,984,939 A | 11/1999 | Yoon |
| 5,776,128 A | 7/1998 | Eggers | 5,989,277 A | 11/1999 | LeMaire, III et al. |
| 5,776,130 A | 7/1998 | Buysse et al. | 5,993,466 A | 11/1999 | Yoon |
| 5,779,646 A | 7/1998 | Koblish et al. | 5,993,467 A | 11/1999 | Yoon |
| 5,779,701 A | 7/1998 | McBrayer et al. | 5,997,565 A | 12/1999 | Inoue |
| H1745 H | 8/1998 | Paraschac | 6,004,332 A | 12/1999 | Yoon et al. |
| 5,792,137 A | 8/1998 | Carr et al. | 6,004,335 A | 12/1999 | Vaitekunas et al. |
| 5,792,165 A | 8/1998 | Klieman et al. | 6,010,516 A | 1/2000 | Hulka et al. |
| 5,792,177 A | 8/1998 | Kaseda | 6,017,358 A | 1/2000 | Yoon et al. |
| 5,797,537 A | 8/1998 | Oberlin et al. | 6,021,693 A | 2/2000 | Feng-Sing |
| 5,797,927 A | 8/1998 | Yoon | 6,024,741 A | 2/2000 | Williamson et al. |
| 5,797,938 A | 8/1998 | Paraschac et al. | 6,024,743 A | 2/2000 | Edwards |
| 5,797,941 A | 8/1998 | Schulze et al. | 6,024,744 A | 2/2000 | Kese et al. |
| 5,797,958 A | 8/1998 | Yoon | 6,027,522 A | 2/2000 | Palmer |
| 5,800,449 A | 9/1998 | Wales | 6,030,384 A | 2/2000 | Nezhat |
| 5,807,393 A | 9/1998 | Williamson, IV et al. | 6,033,399 A | 3/2000 | Gines |
| 5,810,764 A | 9/1998 | Eggers et al. | 6,039,733 A | 3/2000 | Buysse et al. |
| 5,810,805 A | 9/1998 | Sutcu et al. | 6,041,679 A | 3/2000 | Slater et al. |
| 5,810,808 A | 9/1998 | Eggers | 6,050,996 A | 4/2000 | Schmaltz et al. |
| 5,810,811 A | 9/1998 | Yates et al. | 6,053,914 A | 4/2000 | Eggers et al. |
| 5,810,877 A | 9/1998 | Roth et al. | 6,053,933 A | 4/2000 | Balazs et al. |
| 5,814,043 A | 9/1998 | Shapeton | D424,694 S | 5/2000 | Tetzlaff et al. |
| 5,814,054 A | 9/1998 | Kortenbach et al. | D425,201 S | 5/2000 | Tetzlaff et al. |
| 5,817,083 A | 10/1998 | Williamson, IV et al. | 6,059,782 A | 5/2000 | Novak et al. |
| 5,817,119 A | 10/1998 | Klieman et al. | 6,066,139 A | 5/2000 | Ryan et al. |
| 5,820,630 A | 10/1998 | Lind | 6,074,386 A | 6/2000 | Goble et al. |
| 5,824,978 A | 10/1998 | Karasik et al. | 6,077,287 A | 6/2000 | Taylor et al. |
| 5,827,271 A | 10/1998 | Buysse et al. | 6,080,180 A | 6/2000 | Yoon et al. |
| 5,827,279 A | 10/1998 | Hughett et al. | RE36,795 E | 7/2000 | Rydell |
| 5,827,281 A | 10/1998 | Levin | 6,083,223 A | 7/2000 | Baker |
| 5,827,323 A | 10/1998 | Klieman et al. | 6,086,586 A | 7/2000 | Hooven |
| 5,827,548 A | 10/1998 | Lavallee et al. | 6,086,601 A | 7/2000 | Yoon |
| 5,833,690 A | 11/1998 | Yates et al. | 6,090,107 A | 7/2000 | Borgmeier et al. |
| 5,843,080 A | 12/1998 | Fleenor et al. | 6,096,037 A | 8/2000 | Mulier et al. |
| 5,849,022 A | 12/1998 | Sakashita et al. | 6,099,550 A | 8/2000 | Yoon |
| 5,853,412 A | 12/1998 | Mayenberger | 6,102,909 A | 8/2000 | Chen et al. |
| 5,859,527 A | 1/1999 | Cook | 6,106,542 A | 8/2000 | Toybin et al. |
| 5,860,976 A | 1/1999 | Billings et al. | 6,110,171 A | 8/2000 | Rydell |
| 5,876,401 A | 3/1999 | Schulze et al. | 6,113,596 A | 9/2000 | Hooven et al. |
| 5,876,412 A | 3/1999 | Piraka | 6,113,598 A | 9/2000 | Baker |
| 5,882,567 A | 3/1999 | Cavallaro et al. | 6,117,158 A | 9/2000 | Measamer et al. |
| 5,891,141 A | 4/1999 | Rydell | 6,122,549 A | 9/2000 | Sharkey et al. |
| 5,891,142 A | 4/1999 | Eggers et al. | 6,123,701 A | 9/2000 | Nezhat |
| 5,893,863 A | 4/1999 | Yoon | H1904 H | 10/2000 | Yates et al. |
| 5,893,875 A | 4/1999 | O'Connor et al. | 6,126,658 A | 10/2000 | Baker |
| 5,893,877 A | 4/1999 | Gampp, Jr. et al. | 6,126,665 A | 10/2000 | Yoon |
| 5,897,563 A | 4/1999 | Yoon et al. | 6,139,563 A | 10/2000 | Cosgrove, III et al. |
| 5,902,301 A | 5/1999 | Olig | 6,143,005 A | 11/2000 | Yoon et al. |
| 5,906,630 A | 5/1999 | Anderhub et al. | 6,152,923 A | 11/2000 | Ryan |
| 5,908,420 A | 6/1999 | Parins et al. | 6,162,220 A | 12/2000 | Nezhat |
| 5,908,432 A | 6/1999 | Pan | 6,171,316 B1 | 1/2001 | Kovac et al. |
| 5,911,719 A | 6/1999 | Eggers | 6,174,309 B1 | 1/2001 | Wrublewski et al. |
| 5,913,874 A | 6/1999 | Berns et al. | 6,178,628 B1 | 1/2001 | Clemens et al. |
| 5,921,916 A | 7/1999 | Aeikens et al. | 6,179,834 B1 | 1/2001 | Buysse et al. |
| 5,921,984 A | 7/1999 | Sutcu et al. | 6,179,837 B1 | 1/2001 | Hooven |
| 5,925,043 A | 7/1999 | Kumar et al. | 6,183,467 B1 | 2/2001 | Shapeton et al. |
| 5,928,136 A | 7/1999 | Barry | 6,187,003 B1 | 2/2001 | Buysse et al. |
| 5,935,126 A | 8/1999 | Riza | 6,190,386 B1 | 2/2001 | Rydell |
| 5,941,869 A | 8/1999 | Patterson et al. | 6,190,400 B1 | 2/2001 | Vandemoer et al. |
| 5,944,718 A | 8/1999 | Dafforn et al. | 6,193,718 B1 | 2/2001 | Kortenbach et al. |
| 5,951,546 A | 9/1999 | Lorentzen | 6,206,876 B1 | 3/2001 | Levine et al. |
| 5,951,549 A | 9/1999 | Richardson et al. | 6,206,877 B1 | 3/2001 | Kese et al. |
| 5,954,720 A | 9/1999 | Wilson et al. | 6,206,893 B1 | 3/2001 | Klein et al. |
| 5,954,731 A | 9/1999 | Yoon | 6,214,028 B1 | 4/2001 | Yoon et al. |
| 5,954,733 A | 9/1999 | Yoon | 6,217,602 B1 | 4/2001 | Redmon |
| 5,957,923 A | 9/1999 | Hahnen et al. | 6,217,615 B1 | 4/2001 | Sioshansi et al. |
| 5,957,937 A | 9/1999 | Yoon | 6,221,039 B1 | 4/2001 | Durgin et al. |
| 5,960,544 A | 10/1999 | Beyers | 6,223,100 B1 | 4/2001 | Green |
| 5,961,514 A | 10/1999 | Long et al. | 6,224,593 B1 | 5/2001 | Ryan et al. |
| 5,964,758 A | 10/1999 | Dresden | 6,224,614 B1 | 5/2001 | Yoon |
| 5,976,132 A | 11/1999 | Morris | 6,228,080 B1 | 5/2001 | Gines |
| 5,984,932 A | 11/1999 | Yoon | 6,228,083 B1 | 5/2001 | Lands et al. |

| | | |
|---|---|---|
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 8,926,716 | 8/2005 | Baker et al. |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |

| | | |
|---|---|---|
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 * | 2/2009 | Odom et al. .................. 606/51 |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |

| | | |
|---|---|---|
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1* | 5/2005 | Dycus et al. .................. 606/51 |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1* | 5/2005 | Dumbauld et al. ............ 606/45 |
| 2005/0113828 A1* | 5/2005 | Shields et al. ................. 606/51 |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |

| | | | |
|---|---|---|---|
| 2009/0088740 A1 | 4/2009 | Guerra et al. | |
| 2009/0088741 A1 | 4/2009 | Hushka et al. | |
| 2009/0088744 A1 | 4/2009 | Townsend | |
| 2009/0088745 A1 | 4/2009 | Hushka et al. | |
| 2009/0088746 A1 | 4/2009 | Hushka et al. | |
| 2009/0088747 A1 | 4/2009 | Hushka et al. | |
| 2009/0088748 A1 | 4/2009 | Guerra et al. | |
| 2009/0088749 A1 | 4/2009 | Hushka et al. | |
| 2009/0088750 A1 | 4/2009 | Hushka et al. | |
| 2009/0112206 A1 | 4/2009 | Dumbauld et al. | |
| 2009/0131934 A1 | 5/2009 | Odom et al. | |
| 2009/0149853 A1 | 6/2009 | Shields et al. | |
| 2009/0149854 A1 | 6/2009 | Cunningham et al. | |
| 2009/0171350 A1 | 7/2009 | Dycus et al. | |
| 2009/0171353 A1 | 7/2009 | Johnson et al. | |
| 2009/0182327 A1 | 7/2009 | Unger | |
| 2009/0187188 A1 | 7/2009 | Guerra et al. | |

FOREIGN PATENT DOCUMENTS

| | | | |
|---|---|---|---|
| DE | 2415263 | | 10/1975 |
| DE | 2514501 | | 10/1976 |
| DE | 2627679 | | 1/1977 |
| DE | 3612646 | | 4/1987 |
| DE | 8712328 | | 3/1988 |
| DE | 4303882 | | 8/1994 |
| DE | 4403252 | | 8/1995 |
| DE | 19515914 | | 7/1996 |
| DE | 29616210 | | 1/1997 |
| DE | 19608716 | | 4/1997 |
| DE | 19751106 | | 5/1998 |
| DE | 19751108 | | 5/1999 |
| DE | 19738457 | | 1/2009 |
| EP | 0364216 | A1 | 4/1990 |
| EP | 0467501 | | 1/1992 |
| EP | 0518230 | A1 | 12/1992 |
| EP | 0 541 930 | B1 | 5/1993 |
| EP | 0572131 | | 12/1993 |
| EP | 0584787 | A1 | 3/1994 |
| EP | 0589453 | A2 | 3/1994 |
| EP | 0589555 | | 3/1994 |
| EP | 0623316 | A1 | 11/1994 |
| EP | 0624348 | A2 | 11/1994 |
| EP | 0650701 | A1 | 5/1995 |
| EP | 0694290 | A3 | 3/1996 |
| EP | 0717966 | A1 | 6/1996 |
| EP | 0754437 | A3 | 3/1997 |
| EP | 0517243 | | 9/1997 |
| EP | 0853922 | A1 | 7/1998 |
| EP | 0875209 | A1 | 11/1998 |
| EP | 0878169 | A1 | 11/1998 |
| EP | 0887046 | A3 | 1/1999 |
| EP | 0923907 | A1 | 6/1999 |
| EP | 0986990 | A1 | 3/2000 |
| EP | 1034747 | A1 | 9/2000 |
| EP | 1034748 | A1 | 9/2000 |
| EP | 1025807 | A3 | 10/2000 |
| EP | 1034746 | A3 | 10/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1080694 | A1 | 3/2001 |
| EP | 1082944 | A1 | 3/2001 |
| EP | 1159926 | A2 | 12/2001 |
| EP | 1177771 | | 2/2002 |
| EP | 1301135 | A | 4/2003 |
| EP | 1330991 | A1 | 7/2003 |
| EP | 1486177 | A2 | 6/2004 |
| EP | 1472984 | A1 | 11/2004 |
| EP | 0774232 | | 1/2005 |
| EP | 1527747 | A2 | 5/2005 |
| EP | 1530952 | A1 | 5/2005 |
| EP | 1532932 | A1 | 5/2005 |
| EP | 1535581 | A2 | 6/2005 |
| EP | 1609430 | A1 | 12/2005 |
| EP | 1632192 | A1 | 3/2006 |
| EP | 1642543 | | 4/2006 |
| EP | 1645238 | A1 | 4/2006 |
| EP | 1645240 | A2 | 4/2006 |
| EP | 1649821 | | 4/2006 |
| EP | 1707143 | A1 | 10/2006 |
| EP | 1769765 | | 4/2007 |
| EP | 1769766 | | 4/2007 |
| EP | 1929970 | | 6/2008 |
| EP | 1683496 | | 12/2008 |
| GB | 623316 | | 5/1949 |
| GB | 1490585 | | 11/1977 |
| GB | 2214430 | A | 6/1989 |
| GB | 2213416 | | 8/1989 |
| JP | 501068 | | 9/1984 |
| JP | 502328 | | 3/1992 |
| JP | 5-5106 | | 1/1993 |
| JP | 5-40112 | | 2/1993 |
| JP | 06343644 | A2 | 12/1994 |
| JP | 07265328 | A2 | 10/1995 |
| JP | 08056955 | A2 | 3/1996 |
| JP | 08252263 | A2 | 10/1996 |
| JP | 09010223 | A2 | 1/1997 |
| JP | 11244298 | A2 | 9/1999 |
| JP | 2000342599 | A2 | 12/2000 |
| JP | 2000350732 | A2 | 12/2000 |
| JP | 2001008944 | A2 | 1/2001 |
| JP | 2001029356 | A2 | 2/2001 |
| JP | 2001128990 | A2 | 5/2001 |
| SU | SU401367 | | 11/1974 |
| WO | WO89/00757 | | 1/1989 |
| WO | WO 92/04873 | | 4/1992 |
| WO | WO 92/06642 | | 4/1992 |
| WO | WO 93/21845 | | 11/1993 |
| WO | WO 94/08524 | A | 4/1994 |
| WO | WO94/20025 | | 9/1994 |
| WO | WO 95/02369 | | 1/1995 |
| WO | WO95/07662 | | 3/1995 |
| WO | WO 95/07662 | | 3/1995 |
| WO | WO95/15124 | | 6/1995 |
| WO | WO96/05776 | | 2/1996 |
| WO | WO 96/22056 | | 7/1996 |
| WO | WO 96/13218 | | 9/1996 |
| WO | WO 97/00646 | | 1/1997 |
| WO | WO 97/00647 | | 1/1997 |
| WO | WO 97/10764 | | 3/1997 |
| WO | WO97/10764 | | 3/1997 |
| WO | WO 97/24073 | | 7/1997 |
| WO | WO 97/24993 | | 7/1997 |
| WO | WO 98/27880 | | 7/1998 |
| WO | WO 99/03407 | | 1/1999 |
| WO | WO 99/03408 | | 1/1999 |
| WO | WO 99/03409 | | 1/1999 |
| WO | WO 99/12488 | | 3/1999 |
| WO | WO 99/23933 | | 5/1999 |
| WO | WO 99/40857 | | 8/1999 |
| WO | WO 99/40861 | | 8/1999 |
| WO | WO 99/51158 | | 10/1999 |
| WO | WO 99/66850 | A | 12/1999 |
| WO | WO 00/24330 | | 5/2000 |
| WO | WO 00/24331 | | 5/2000 |
| WO | WO00/24331 | | 5/2000 |
| WO | WO 00/36986 | | 6/2000 |
| WO | WO 00/41638 | | 7/2000 |
| WO | WO00/47124 | | 8/2000 |
| WO | WO 00/53112 | | 9/2000 |
| WO | WO 01/17448 | A | 3/2001 |
| WO | WO 01/54604 | | 8/2001 |
| WO | WO02/07627 | | 1/2002 |

| | | |
|---|---|---|
| WO | WO 02/07627 | 1/2002 |
| WO | WO 02/067798 A1 | 9/2002 |
| WO | WO 02/080783 | 10/2002 |
| WO | WO02/080783 | 10/2002 |
| WO | WO 02/080784 | 10/2002 |
| WO | WO02/080784 | 10/2002 |
| WO | WO02/080785 | 10/2002 |
| WO | WO 02/080785 | 10/2002 |
| WO | WO 02/080786 | 10/2002 |
| WO | WO02/080786 | 10/2002 |
| WO | WO02/080793 | 10/2002 |
| WO | WO 02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
International Search Report EP 07021647.8 dated May 2, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy at al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds In Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With the LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.

McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7. dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

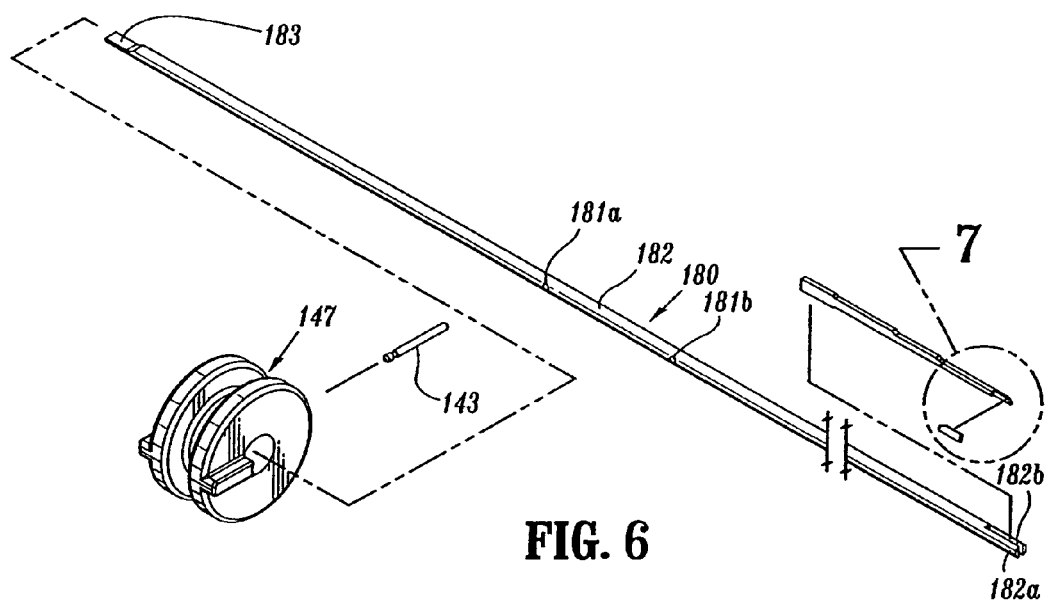
FIG. 6
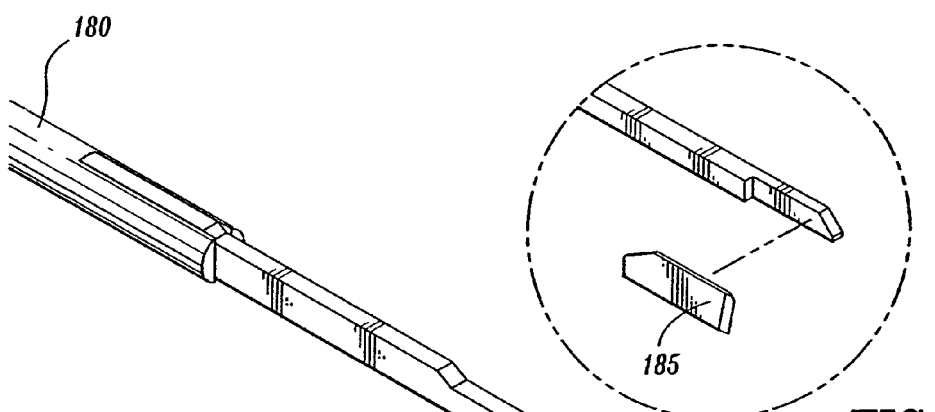
FIG. 8          FIG. 7
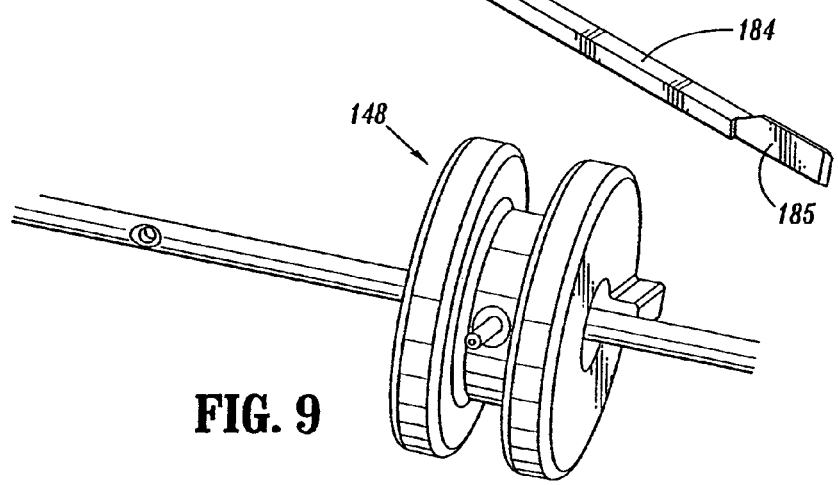
FIG. 9

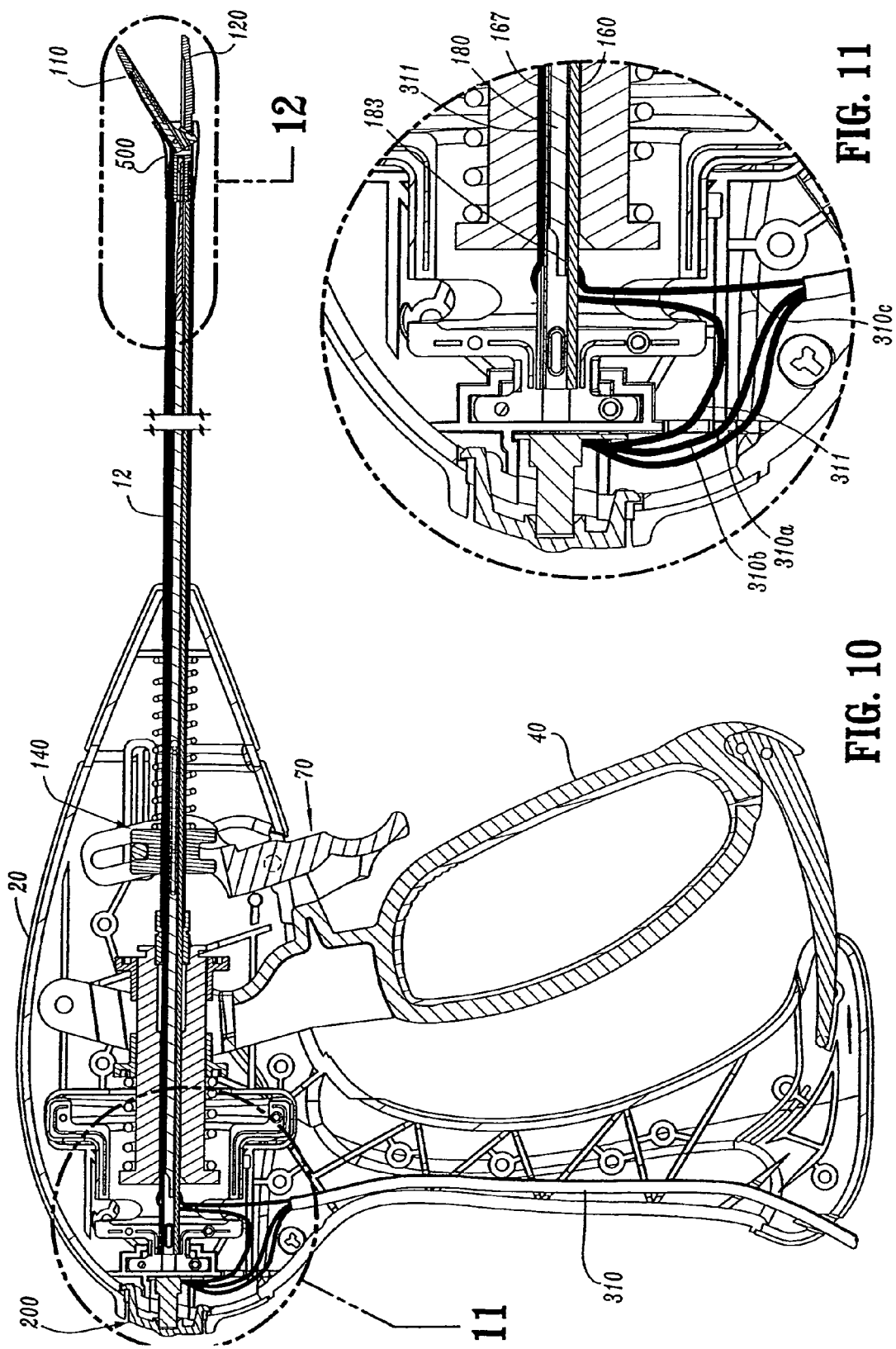

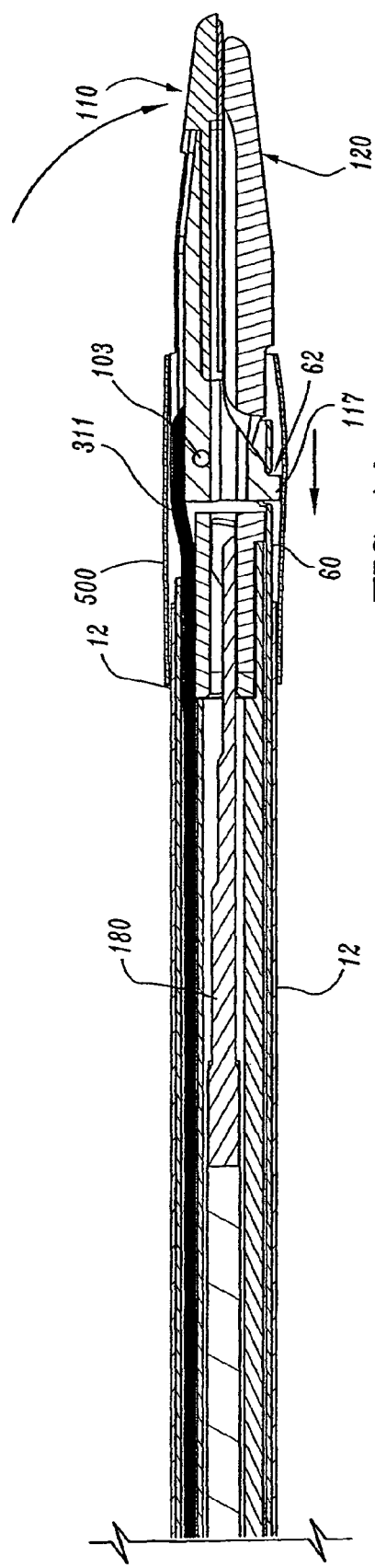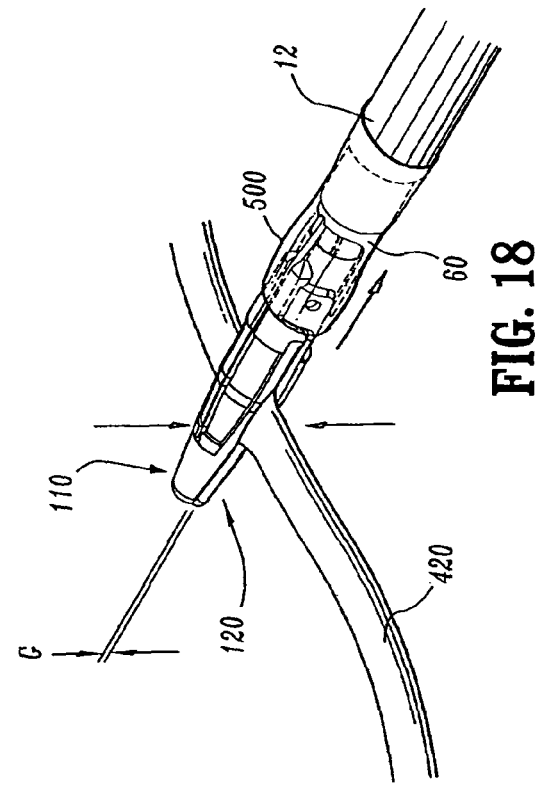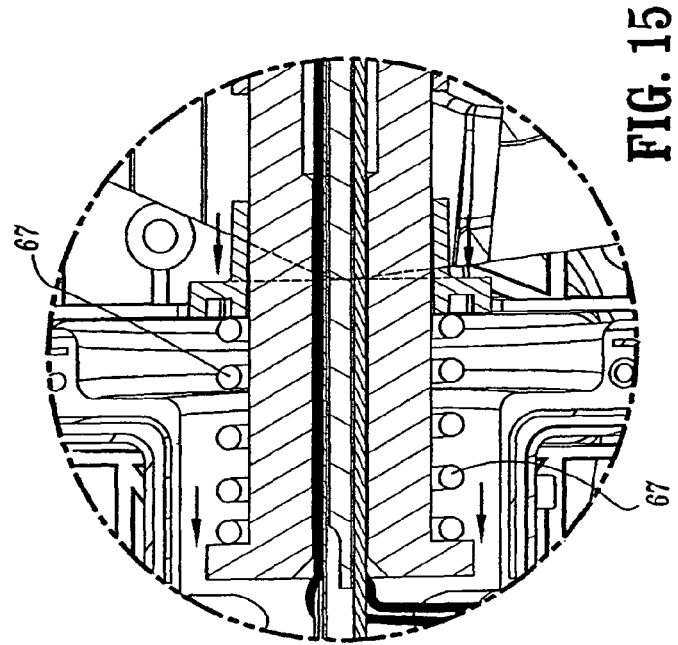

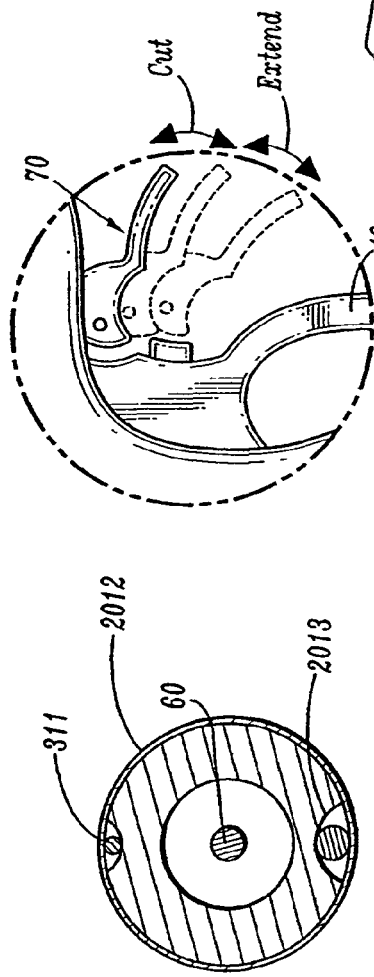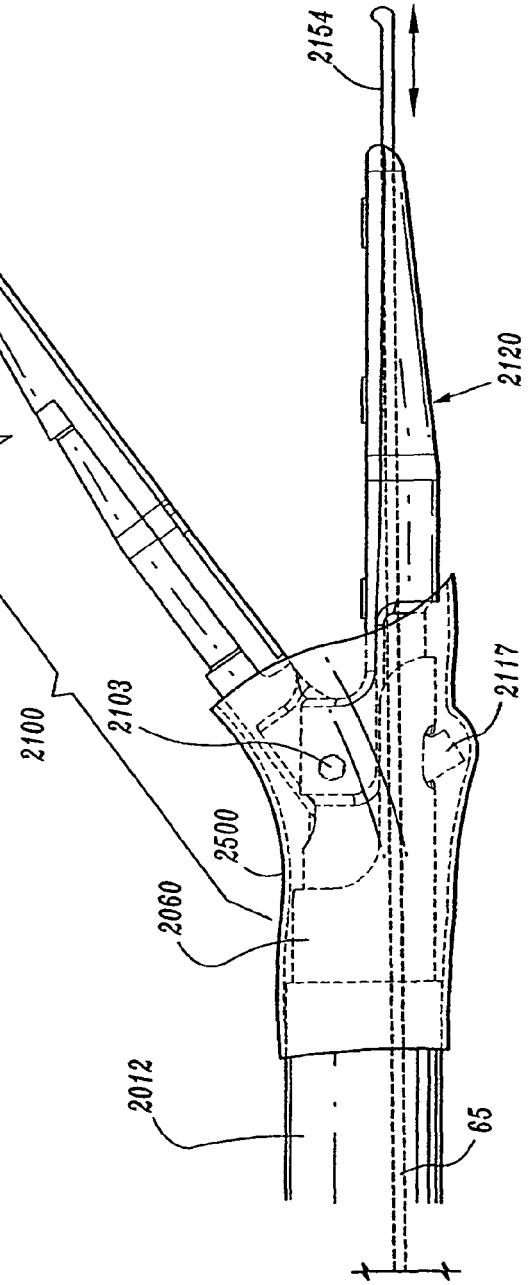

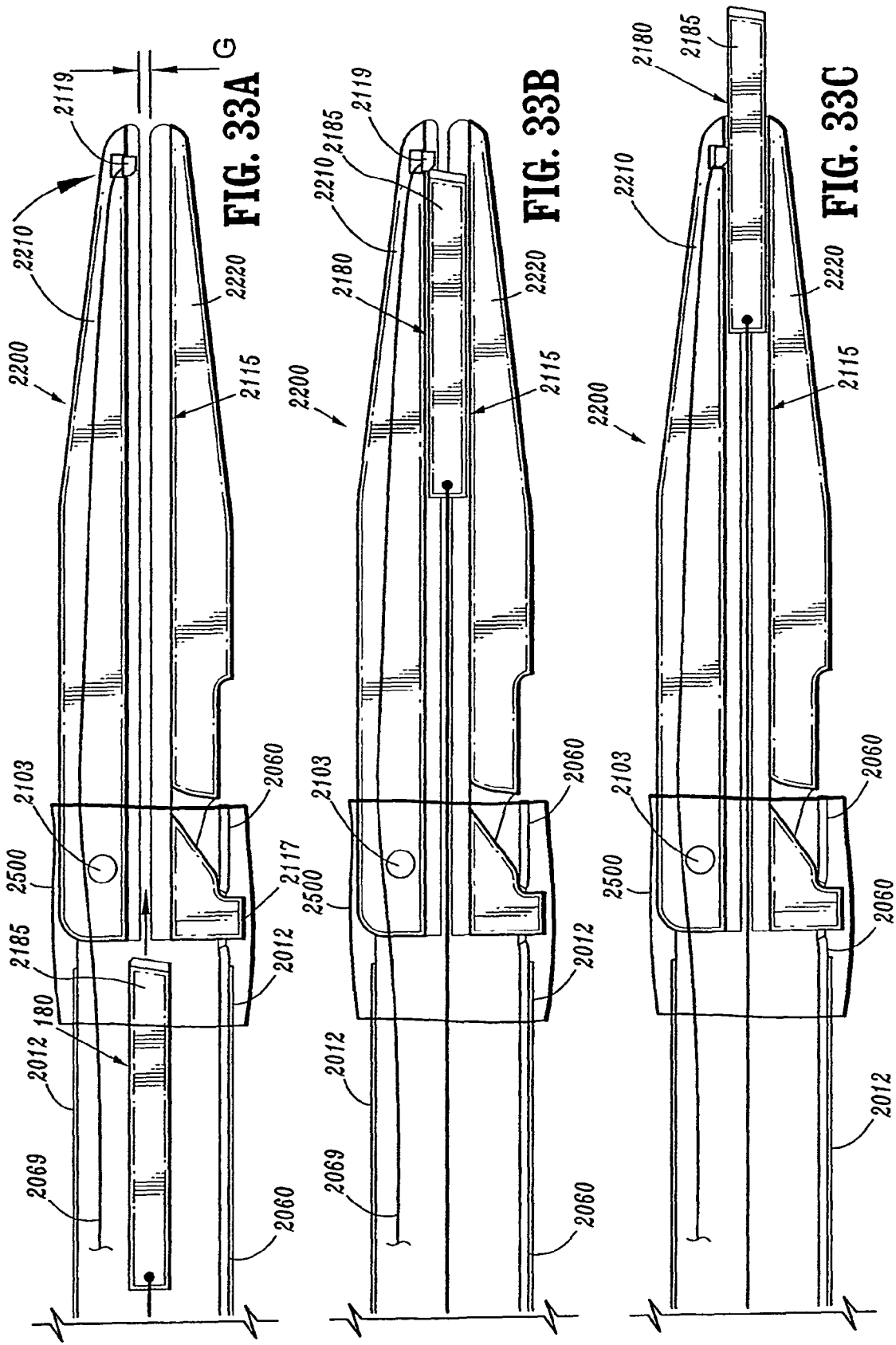

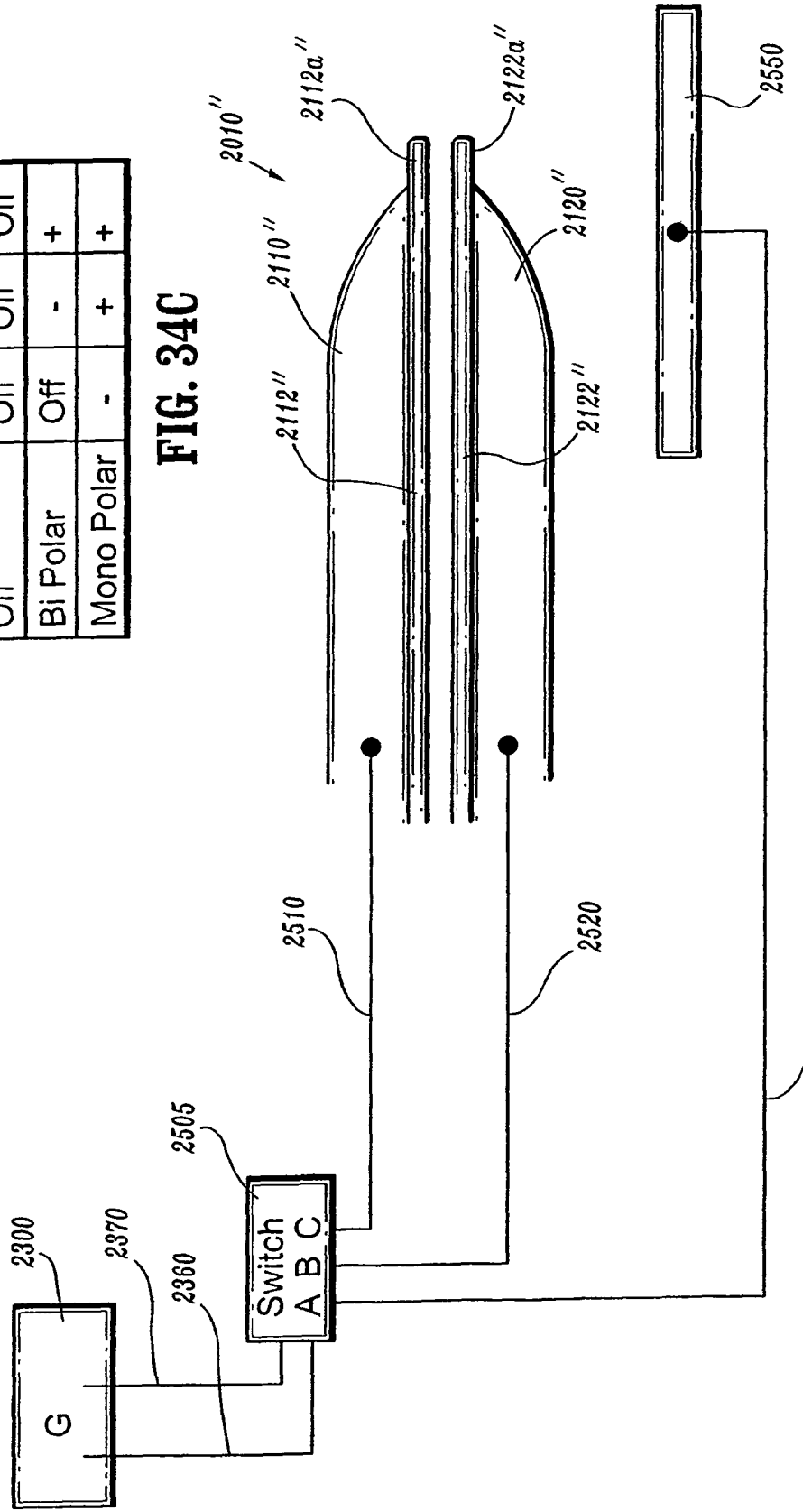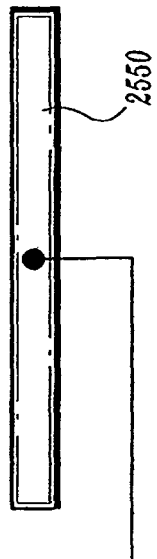

INSULATING BOOT FOR ELECTROSURGICAL FORCEPS

CROSS-REFERENCE TO RELATED APPLICATIONS

This application claims the benefit of priority of U.S. Provisional Patent Application Ser. No. 60/722,213 by Scott DePierro et al., entitled "INSULATING BOOT FOR ELECTROSURGICAL FORCEPS" filed on Sep. 30, 2005, now U.S. patent application Ser. No. 11/529,798 published as U.S. Patent Application Publication No. US2007/0078458 A1, the entire contents of which is incorporated by reference herein. This application cross-references U.S. Provisional Patent Application Ser. No. 60/722,186 by Paul Guerra, entitled "METHOD FOR MANUFACTURING AN END EFFECTOR ASSEMBLY," filed on Sep. 30, 2005, now U.S. patent application Ser. No. 11/529,414 published as U.S. Patent Application Publication No. US2007/0074807 A1 and U.S. Provisional Patent Application Ser. No. 60/722,359 by Kristin Johnson et al, entitled "FLEXIBLE ENDOSCOPIC CATHETER WITH LIGASURE," [[both]] filed on Sep. 30, 2005, now U.S. patent application Ser. No. 11/540,779 published as U.S. Patent Application Publication No. US2007/0078559A1, the entire contents of both applications being incorporated by reference herein.

BACKGROUND

1. Technical Field

The present disclosure relates to an insulated electrosurgical forceps and more particularly, the present disclosure relates to an insulating boot for use with either an endoscopic or open bipolar and/or monopolar electrosurgical forceps for sealing, cutting, and/or coagulating tissue.

2. Background of Related Art

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters must be accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches (about 0.03 mm to about 0.15 mm). Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

Many known instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied the tissue may pre-maturely move prior to activation and sealing and/or a thicker, less reliable seal may be created.

As mentioned above, in order to properly and effectively seal larger vessels or tissue, a greater closure force between opposing jaw members is required. It is known that a large closure force between the jaws typically requires a large moment about the pivot for each jaw. This presents a design challenge because the jaw members are typically affixed with pins which are positioned to have small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure. As can be appreciated, if metal pivot pins are employed, the metal pins must be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the tissue during compression and prior to activation. As a result thereof, providing an instrument which consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to uniformly, consistently and effectively seal the vessel. In other words, the success of the seal would greatly depend upon the ultimate skill of the surgeon rather than the efficiency of the instrument.

It has been found that the pressure range for assuring a consistent and effective seal is between about 3 $kg/cm^2$ to about 16 $kg/cm^2$ and, preferably, within a working range of 7 $kg/cm^2$ to 13 $kg/cm^2$. Manufacturing an instrument which is capable of providing a closure pressure within this working range has been shown to be effective for sealing arteries, tissues and other vascular bundles.

Various force-actuating assemblies have been developed in the past for providing the appropriate closure forces to effect vessel sealing. For example, one such actuating assembly has been developed by Valleylab Inc., a division of Tyco Healthcare LP, for use with Valleylab's vessel sealing and dividing instrument commonly sold under the trademark LIGASURE ATLAS®. This assembly includes a four-bar mechanical linkage, a spring and a drive assembly which cooperate to consistently provide and maintain tissue pressures within the above working ranges. The LIGASURE ATLAS® is presently designed to fit through a 10 mm cannula and includes a bi-lateral jaw closure mechanism which is activated by a foot switch. A trigger assembly extends a knife distally to separate the tissue along the tissue seal. A rotating mechanism is associated with distal end of the handle to allow a surgeon to selectively rotate the jaw members to facilitate grasping tissue. U.S. Pat. Nos. 7,101,371 and 7,083,618 and PCT Application Ser. Nos. PCT/US01/01890 PCT/US02/01890, now WO 2002/080799, and PCT/US01/11340, now WO 2002/080795, describe in detail the operating features of the LIGASURE ATLAS® and various methods relating thereto. Co-pending U.S. application Ser. No. 10/970,307, now U.S. Pat. No. 7,232,440, relates to another version of an endoscopic forceps sold under the trademark LIGASURE V® by Valleylab, Inc., a division of Tyco Healthcare, LP. In addition, commonly owned, U.S. patent application Ser. No. 10/873,860, filed on Jun. 22, 2004 and entitled "Open Vessel Sealing Instrument with Cutting Mechanism and Distal Lockout", now U.S. Pat. No. 7,252,667, and incorporated by reference in its entirety herein discloses an open forceps which is configured to seal and cut tissue which can be configured to include one or more of the presently disclosed embodiments described herein. The entire contents of all of these applications are hereby incorporated by reference herein.

For example, the commonly owned U.S. patent application Ser. No. 10/970,307 filed on Oct. 21, 2004 and entitled "Bipolar Forceps Having Monopolar Extension", now U.S. Pat. No. 7,232,440, discloses an electrosurgical forceps for coagulating, sealing, and/or cutting tissue having a selectively energizable and/or extendable monopolar extension for enhanced electrosurgical effect. The instrument includes a monopolar element which may be selectively extended and selectively activated to treat tissue. Various different designs are envisioned which allow a user to selectively energize tissue in a bipolar or monopolar mode to seal or coagulate tissue depending upon a particular purpose. Some of the various designs include: (1) a selectively extendable and energizable knife design which acts as a monopolar element; (2) a bottom jaw which is electrically and selectively configured to act as a monopolar element; (3) tapered jaw members having distal ends which are selectively energized with a single electrical potential to treat tissue in a monopolar fashion; and (4) other configurations of the end effector assembly and/or bottom or second jaw member which are configured to suit a particular purpose or to achieve a desired surgical result.

However, a general issue with existing electrosurgical forceps is that the jaw members rotate about a common pivot at the distal end of a metal or otherwise conductive shaft such that there is potential for both the jaws, a portion of the shaft, and the related mechanism components to conduct electrosurgical energy (either monopolar or as part of a bipolar path) to the patient tissue. Existing electrosurgical instruments with jaws either cover the pivot elements with an inflexible shrink-tube or do not cover the pivot elements and connection areas and leave these portions exposed.

SUMMARY

It would be desirous to provide electrosurgical instruments with a flexible insulating boot that both permits pivoting and other associated movements of the jaw members and also reduces the potential for stray or miscellaneous currents affecting surrounding tissue.

The present disclosure relates to an electrosurgical forceps having a shaft with jaw members at a distal end thereof. The jaw members are movable about a pivot by actuation of a drive assembly that moves the jaw members from a first position wherein the jaw members are disposed in spaced relation relative to one another to a second position wherein the jaw members are closer to one another for grasping and treating tissue. The forceps also includes a movable handle that actuates the drive assembly to move the jaw members relative to one another.

At least one jaw member is adapted to connect to a source of electrical energy such that at least one of the jaw members is capable of conducting energy to tissue held therebetween to treat tissue. A flexible insulating boot is disposed on at least a portion of an exterior surface of at least one jaw member. The insulating boot is configured and made from a material that insulates tissue from various exposed areas of the shaft and the jaw members.

In one particularly useful embodiment, one end of the insulating boot is disposed on at least a portion of an exterior surface of the shaft and another end of the insulating boot is disposed on at least a portion of an exterior surface of at least one jaw member proximate the pivot such that movement of the jaw members is substantially unimpeded. In another embodiment according to the present disclosure, the insulating boot is made of at least one of a viscoelastic, elastomeric, and flexible material suitable for use with a sterilization process that does not substantially impair structural integrity of the boot. In particular, the sterilization process may include ethylene oxide.

The jaw members (or jaw member) may also include a series of stop members disposed thereon for regulating distance between the jaw members such that a gap is created between the jaw members during the sealing process.

The forceps may also include a knife that is selectively deployable to cut tissue disposed between the jaw members.

In one embodiment, the jaw members are configured to treat tissue in a monopolar fashion, while in another embodiment, the jaw members are configured to treat tissue in a bipolar fashion.

In one embodiment of the present disclosure, the present disclosure is directed to an electrosurgical forceps for sealing tissue having a pair of first and second shaft members each with a jaw member disposed at a distal end thereof. The jaw members are movable about a pivot from a first position in spaced relation relative to one another to at least one subsequent position wherein the jaw members cooperate to grasp tissue therebetween. At least one of the jaw members includes an electrically conductive sealing plate adapted to communicate electrosurgical energy to tissue held therebetween and a flexible insulating boot disposed on at least a portion of an exterior surface of at least one jaw member.

In yet another useful embodiment, the present disclosure relates to an electrosurgical forceps having a housing with a shaft affixed thereto. The shaft includes first and second jaw members attached to a distal end thereof. The forceps includes an actuator for moving jaw members relative to one another from a first position wherein the jaw members are disposed in spaced relation relative to one another to a second position wherein the jaw members cooperate to grasp tissue therebetween. Each jaw member is adapted to connect to a source of electrosurgical energy such that the jaw members are selectively capable of conducting energy to tissue held therebetween to treat tissue.

The forceps also includes a knife that is selectively moveable within a knife channel defined within at least one of the jaw members to cut tissue disposed therebetween. A monopolar element is housed within at least one jaw member and is selectively movable from a first proximal position within the jaw members to a second distal position within the jaw member(s). The monopolar element may be connected to the source of electrosurgical energy and may be selectively activatable independently of the jaw members. The forceps includes a flexible insulating boot disposed on at least a portion of at least one jaw member.

BRIEF DESCRIPTION OF THE DRAWINGS

Various embodiments of the subject instrument are described herein with reference to the drawings wherein:

FIG. 6 is an enlarged, perspective view of the knife assembly with parts separated;

FIG. 7 is an enlarged view of the indicated area of detail of FIG. 6 showing a knife blade of the knife assembly;

FIG. 8 is a greatly-enlarged, perspective view of a distal end of the knife assembly;

FIG. 9 is a greatly-enlarged, perspective view of a knife drive of the knife assembly;

FIG. 10 is a cross-section of the housing with the end effector shown in open configuration having the insulating boot of the present disclosure and showing the internal, electrical routing of an electrosurgical cable and electrical leads;

FIG. 11 is a greatly-enlarged view of the indicated area of detail of FIG. 10;

FIG. 14 is a greatly-enlarged view of the indicated area of detail in FIG. 13;

FIG. 15 is a greatly-enlarged view of the indicated area of detail in FIG. 13;

FIG. 18 is an enlarged, rear, perspective view of the end effectors shown grasping tissue;

FIG. 27 is an enlarged, cross section taken along line 27-27 of FIG. 26;

FIG. 28 is an enlarged, side view of the trigger assembly of FIG. 26;

FIG. 29 is an enlarged, side view of the embodiment of an end effector assembly of FIG. 26 having the insulating boot according to the present disclosure and showing relative extension of a monopolar element from a distal end of the end effector assembly;

FIG. 33A is an enlarged, side schematic view of one embodiment of an end effector assembly having the insulating boot according to the present disclosure and showing relative movement of a first jaw member relative to a second jaw member prior to advancement of the knife through the end effector assembly;

FIG. 33B is an enlarged, side schematic view of the end effector assembly showing relative movement of the knife through the end effector assembly to divide tissue;

FIG. 33C is an enlarged, side schematic view of the end effector assembly showing relative movement of the knife extending from the distal end of the end effector assembly;

FIG. 34B is schematic view of another embodiment of an end effector assembly capable of being configured with the insulating boot according to the present disclosure and showing a series of electrical connections to a control switch and a generator to enable both bipolar activation and monopolar activation;

FIG. 34C is a table showing the various modes of operation of the forceps utilizing the end effector configuration of FIG. 34B;

DETAILED DESCRIPTION

Figure 1:
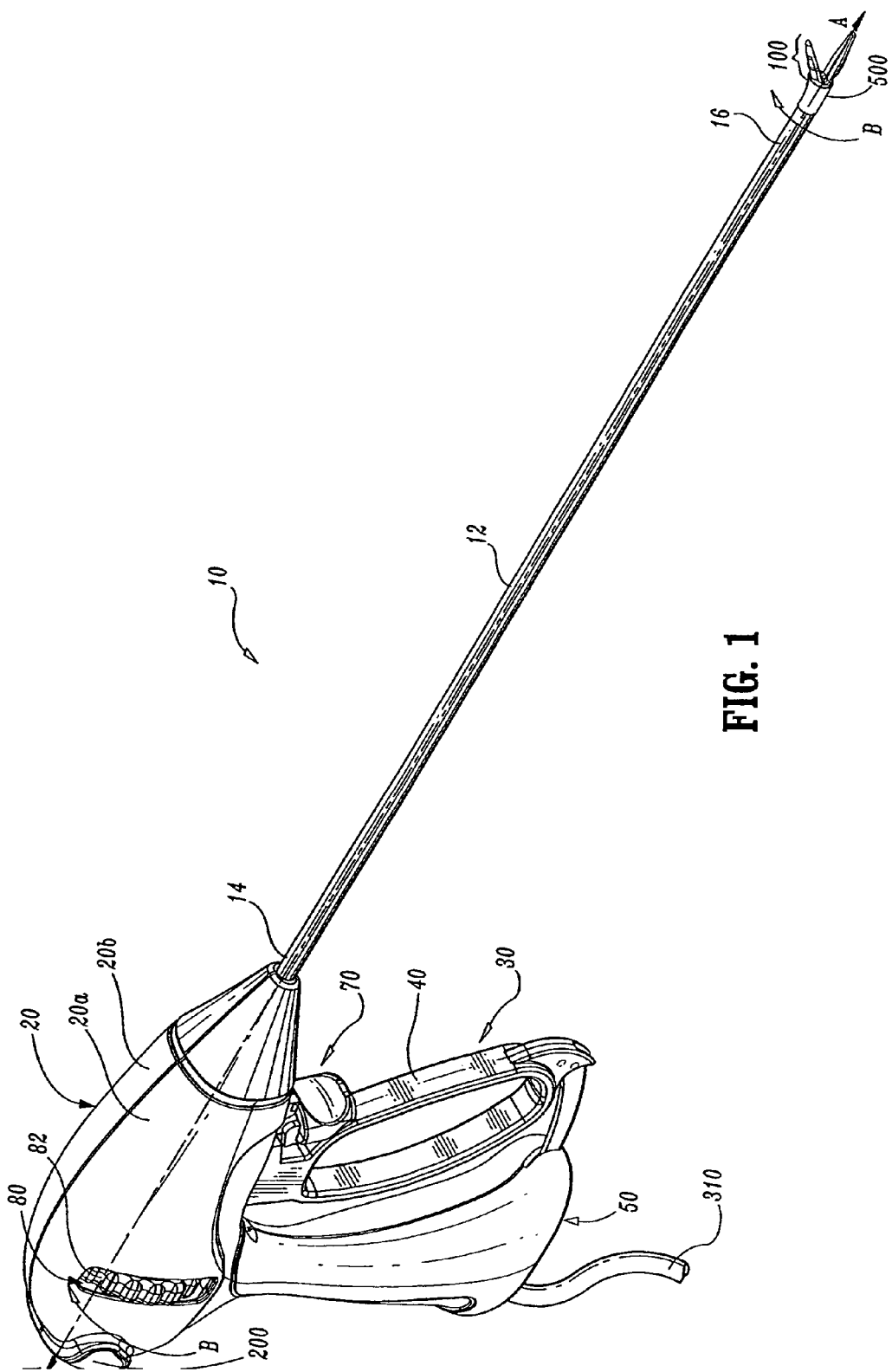
FIG. 1 is a left, perspective view of one version of the present disclosure that includes an endoscopic bipolar forceps showing a housing, a shaft and an end effector assembly having an insulating boot according to the present disclosure.
Figure 2:
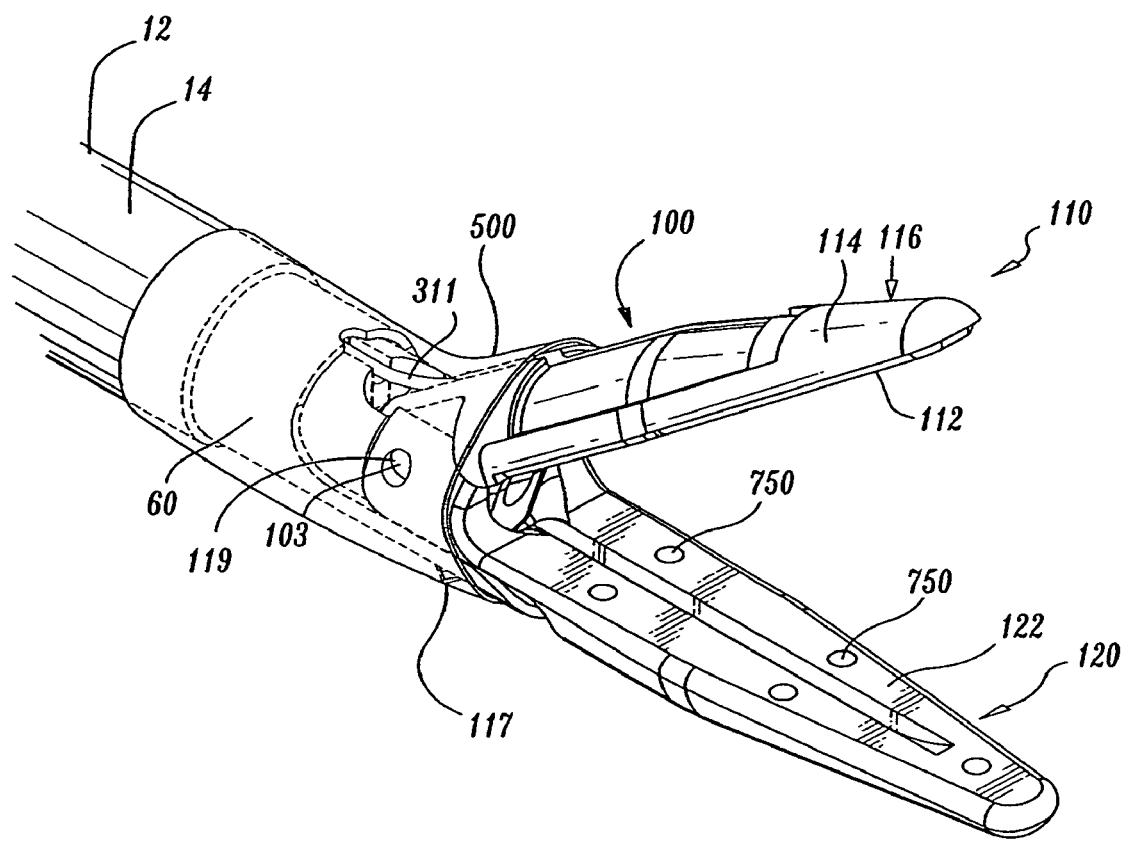
FIG. 2 is an enlarged, left perspective view of the end effector assembly with the jaw members shown in open configuration having the insulating boot according to the present disclosure.
Figure 3:
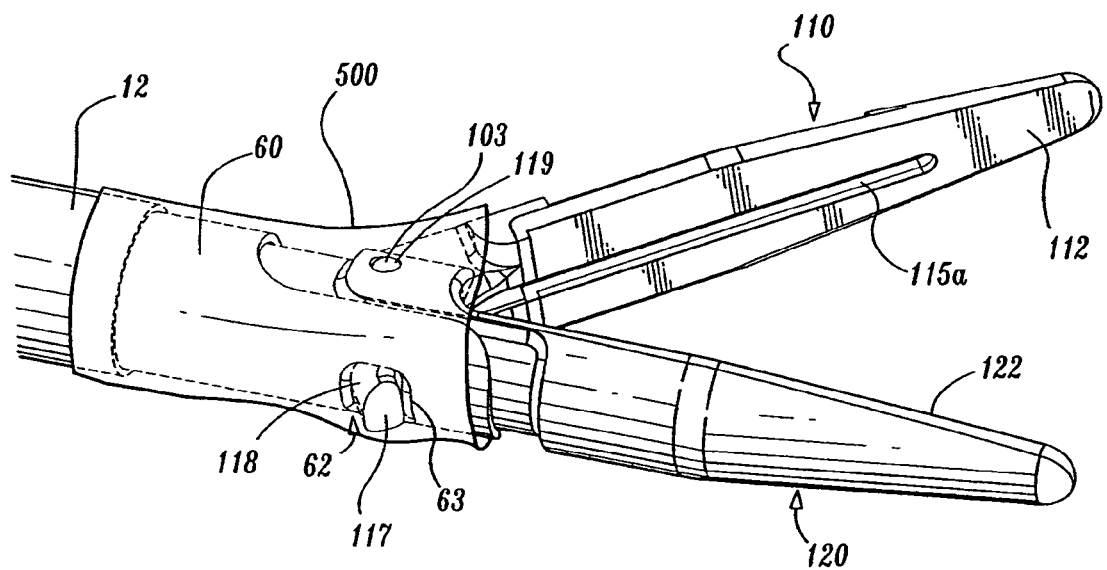
FIG. 3 is a full perspective view of the end effector assembly of FIG. 1 having the insulating boot according to the present disclosure.
Figure 19:
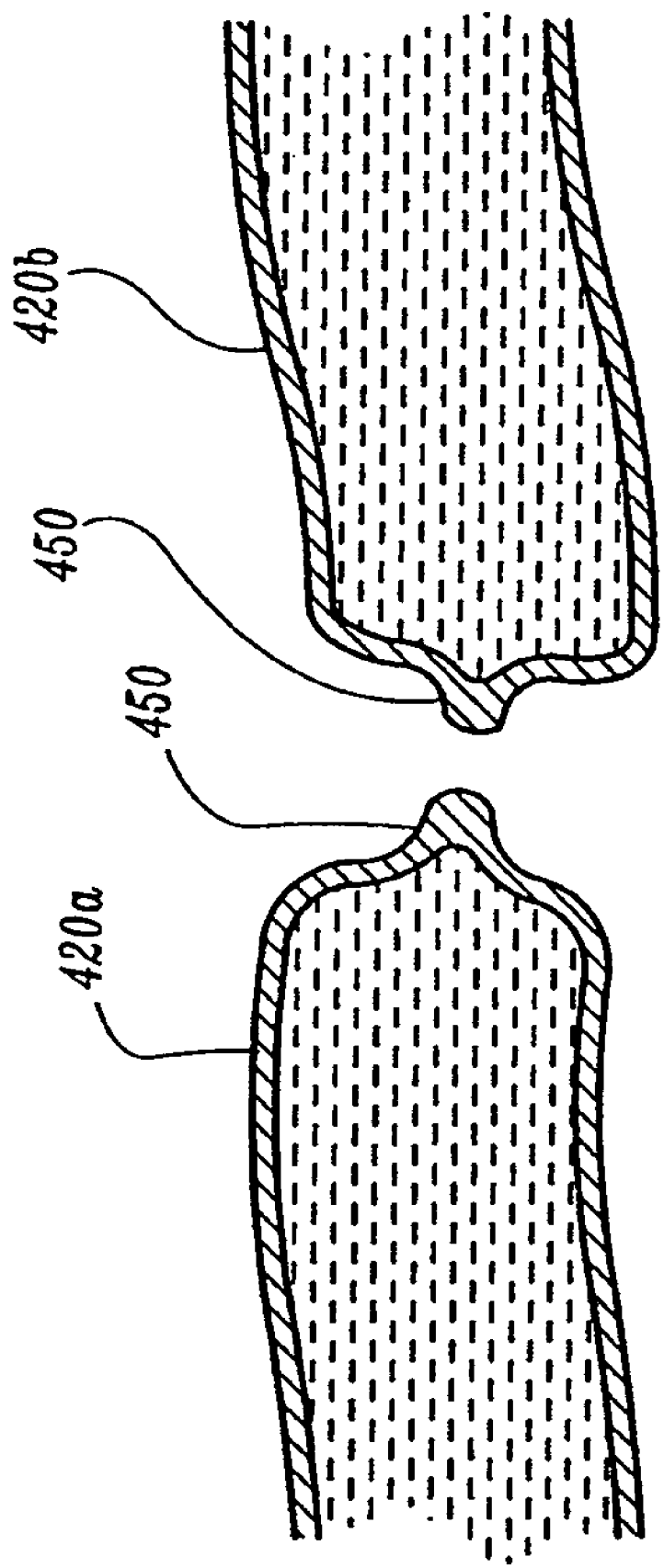
FIG. 19 is a side, cross section of a tissue seal after separation by the knife assembly.

Referring initially to FIGS. 1-3, one particularly useful endoscopic forceps 10 is shown for use with various surgical procedures and generally includes a housing 20, a handle assembly 30, a rotating assembly 80, a trigger assembly 70, a knife assembly and an end effector assembly 100 that mutually cooperate to grasp, seal and divide tubular vessels and vascular tissue 420 (see FIGS. 18-19). For the purposes herein, forceps 10 will be described generally. However, the various particular aspects of this particular forceps are detailed in commonly owned U.S. patent application Ser. No. 10/460,926, filed on Jun. 13, 2003, and entitled "VESSEL SEALER AND DIVIDER FOR USE WITH SMALL TROCARS AND CANNULAS," now U.S. Pat. No. 7,156,846, and previously mentioned U.S. patent application Ser. No. 10/970,307, now U.S. Pat. No. 7,232,440, the entire contents of each of which are incorporated by reference herein. Forceps 10 includes a shaft 12 that has a distal end 16 dimensioned to mechanically engage the end effector assembly 100 and a proximal end 14 that mechanically engages the housing 20. As will be discussed in more detail below, the end effector assembly 100 includes a flexible insulating boot 500 configured to cover at least a portion of the exterior surfaces of the end effector assembly 100.

Forceps 10 also includes an electrosurgical cable 310 that connects the forceps 10 to a source of electrosurgical energy, e.g., a generator (not shown). The generator includes various safety and performance features including isolated output, independent activation of accessories, and Instant Response™ technology (a proprietary technology of Valleylab, Inc., a division of Tyco Healthcare, LP) that provides an advanced feedback system to sense changes in tissue many times per second and adjust voltage and current to maintain appropriate power. Cable 310 is internally divided into cable lead 310a, 310b and 310c that each transmit electrosurgical energy through their respective feed paths through the forceps 10 to the end effector assembly 100. (See FIG. 11).

Handle assembly 30 includes a fixed handle 50 and a movable handle 40. Fixed handle 50 is integrally associated with housing 20 and handle 40 is movable relative to fixed handle 50. Rotating assembly 80 is integrally associated with the housing 20 and is rotatable approximately 180 degrees in either direction about a longitudinal axis "A" (See FIG. 1). Details of the rotating assembly 80 are described in more detail below.

Figure 4:
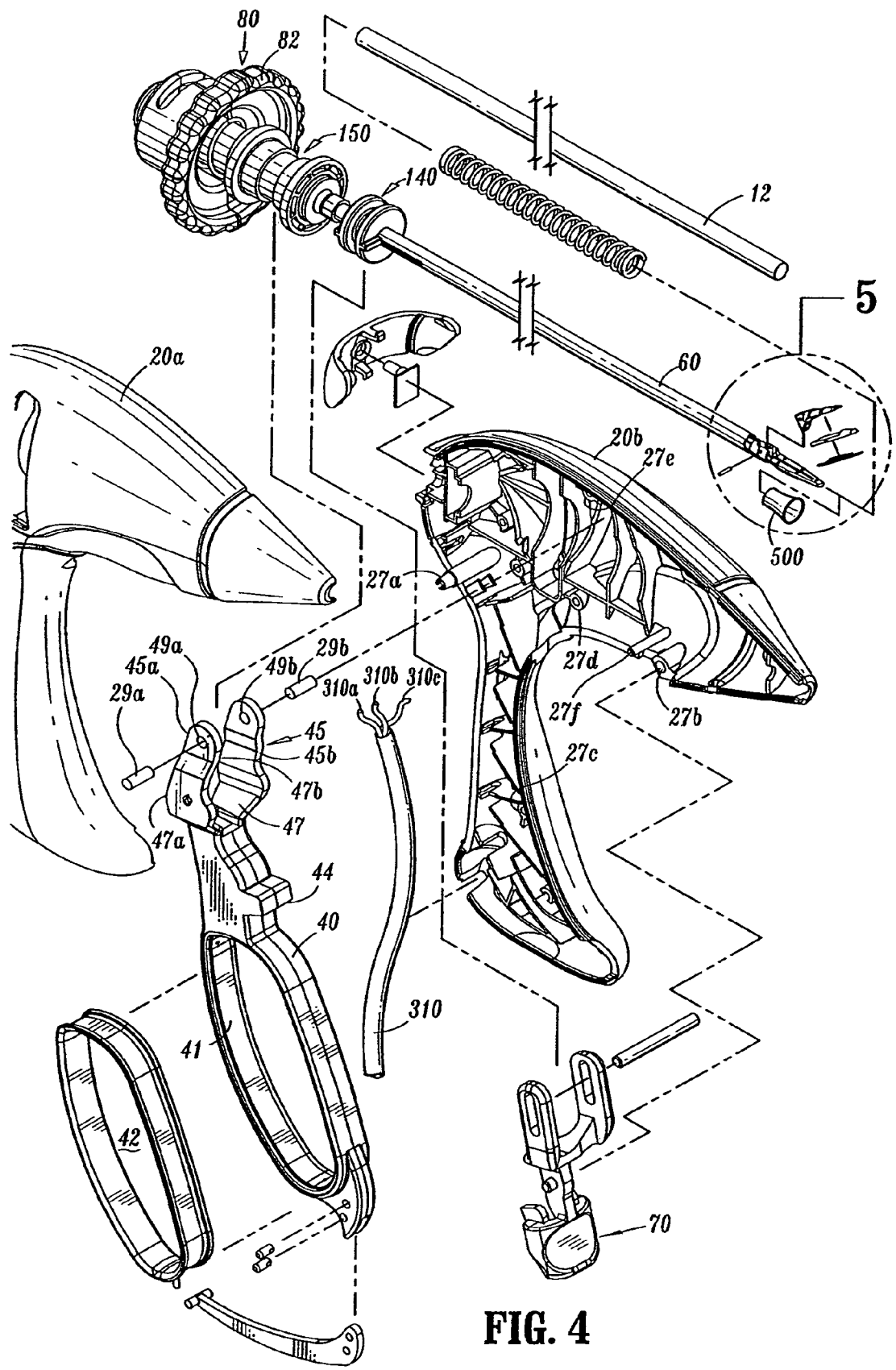
FIG. 4 is an exploded top, perspective view of the housing and internal working components thereof of the endoscopic bipolar forceps of FIG. 1 with parts separated.

As best seen in FIGS. 1 and 4, housing 20 is formed from two (2) housing halves 20a and 20b that each include a plurality of interfaces 27a-27f that are dimensioned to mechanically align and engage one another to form housing 20 and enclose the internal working components of forceps 10. Fixed handle 50 that, as mentioned above, is integrally associated with housing 20, takes shape upon the assembly of the housing halves 20a and 20b. Movable handle 40 and trigger assembly 70 are of unitary construction and are operatively connected to the housing 20 and the fixed handle 50 during the assembly process. Rotating assembly 80 includes two halves that, when assembled, form a knurled wheel 82 that, in turn, houses a drive assembly 150 and a knife assembly 140.

As mentioned above, end effector assembly 100 is attached at the distal end 14 of shaft 12 and includes a pair of opposing jaw members 110 and 120. Movable handle 40 of handle assembly 30 is ultimately connected to the drive assembly 150 that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. All of these components and features are best explained in detail in the above-identified commonly owned U.S. application Ser. No. 10/460,926, now U.S. Pat. No. 7,156,846.

Turning now to the more detailed features of the present disclosure as described with respect to FIGS. 1-4, movable handle 40 includes a finger loop 41 that has an aperture 42 defined therethrough that enables a user to grasp and move the handle 40 relative to the fixed handle 50. As best seen in FIG. 4, movable handle 40 is selectively moveable about a pair of pivot pins 29a and 29b from a first position relative to fixed handle 50 to a second position in closer proximity to the fixed handle 50 that, as explained below, imparts movement of the jaw members 110 and 120 relative to one another. The movable handle include a clevis 45 that forms a pair of upper flanges 45a and 45b each having an aperture 49a and 49b, respectively, at an upper end thereof for receiving the pivot pins 29a and 29b therethrough and mounting the upper end of the handle 40 to the housing 20. In turn, each pin 29a and 29b mounts to a respective housing half 20a and 20b.

Each upper flange 45a and 45b also includes a force-actuating flange or drive flange 47a and 47b, respectively, each of which is aligned along longitudinal axis "A" and which abut the drive assembly 150 such that pivotal movement of the handle 40 forces actuating flange against the drive assembly 150 that, in turn, closes the jaw members 110 and 120.

Movable handle 40 is designed to provide a distinct mechanical advantage over conventional handle assemblies due to the unique position of the pivot pins 29a and 29b (i.e., pivot point) relative to the longitudinal axis "A" of the shaft 12 and the disposition of the driving flange 47 along longitudinal axis "A". In other words, by positioning the pivot pins 29a and 29b above the driving flange 47, the user gains lever-like mechanical advantage to actuate the jaw members 110 and 120 enabling the user to close the jaw members 110 and 120 with lesser force while still generating the required forces necessary to effect a proper and effective tissue seal.

Figure 5:
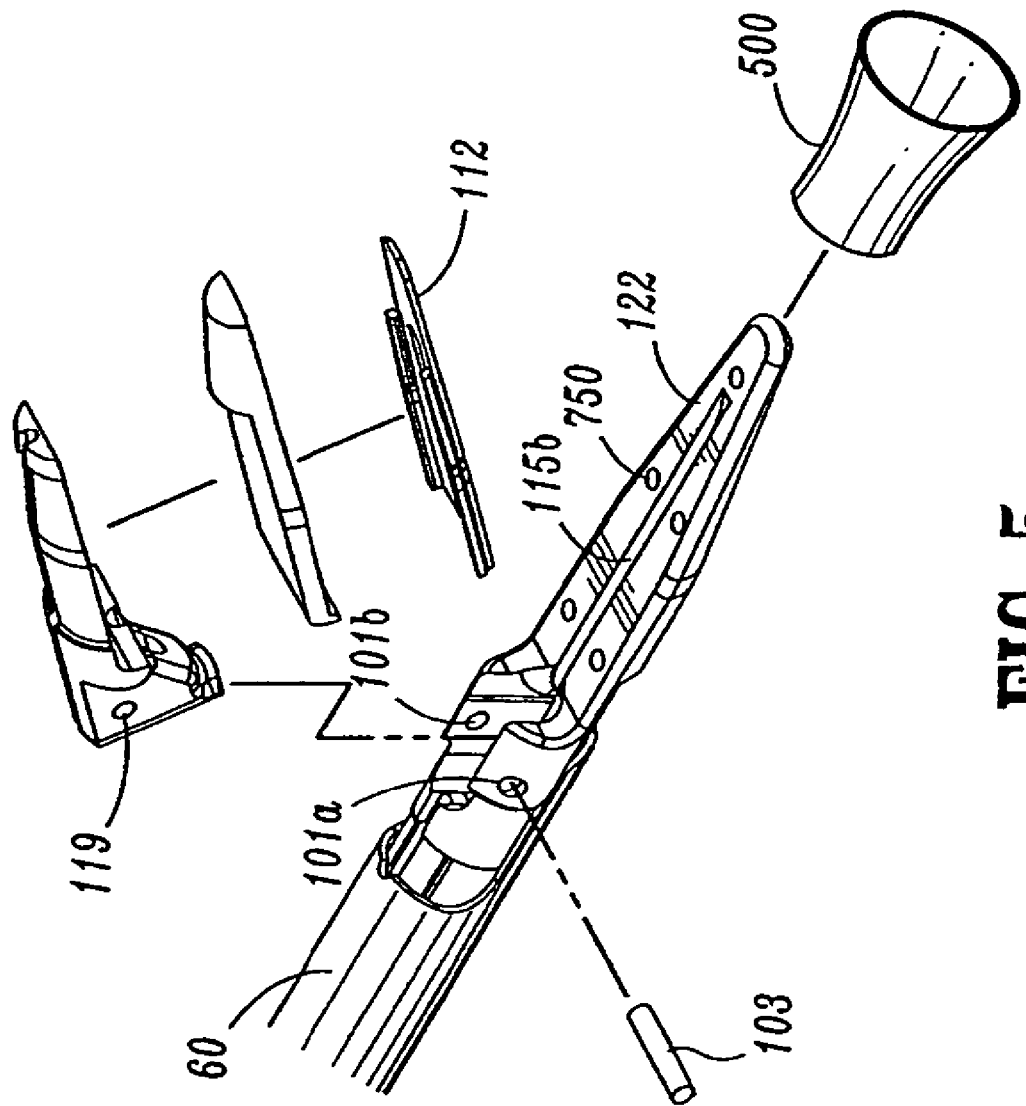
FIG. 5 is an enlarged, top, perspective view of the end effector assembly having the insulating boot of the present disclosure with parts separated.
Figure 12:
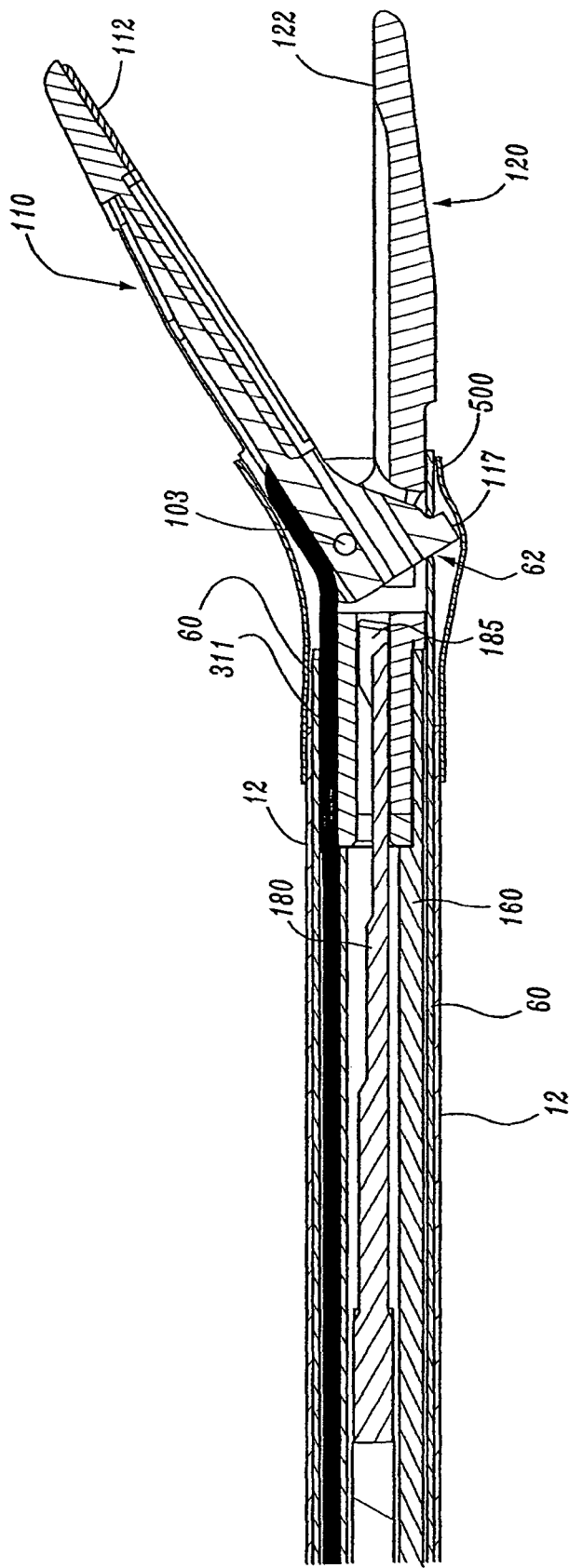
FIG. 12 is a side, cross section of the shaft and end effector assembly with the end effector assembly having the insulating boot of the present disclosure.
Figure 13:
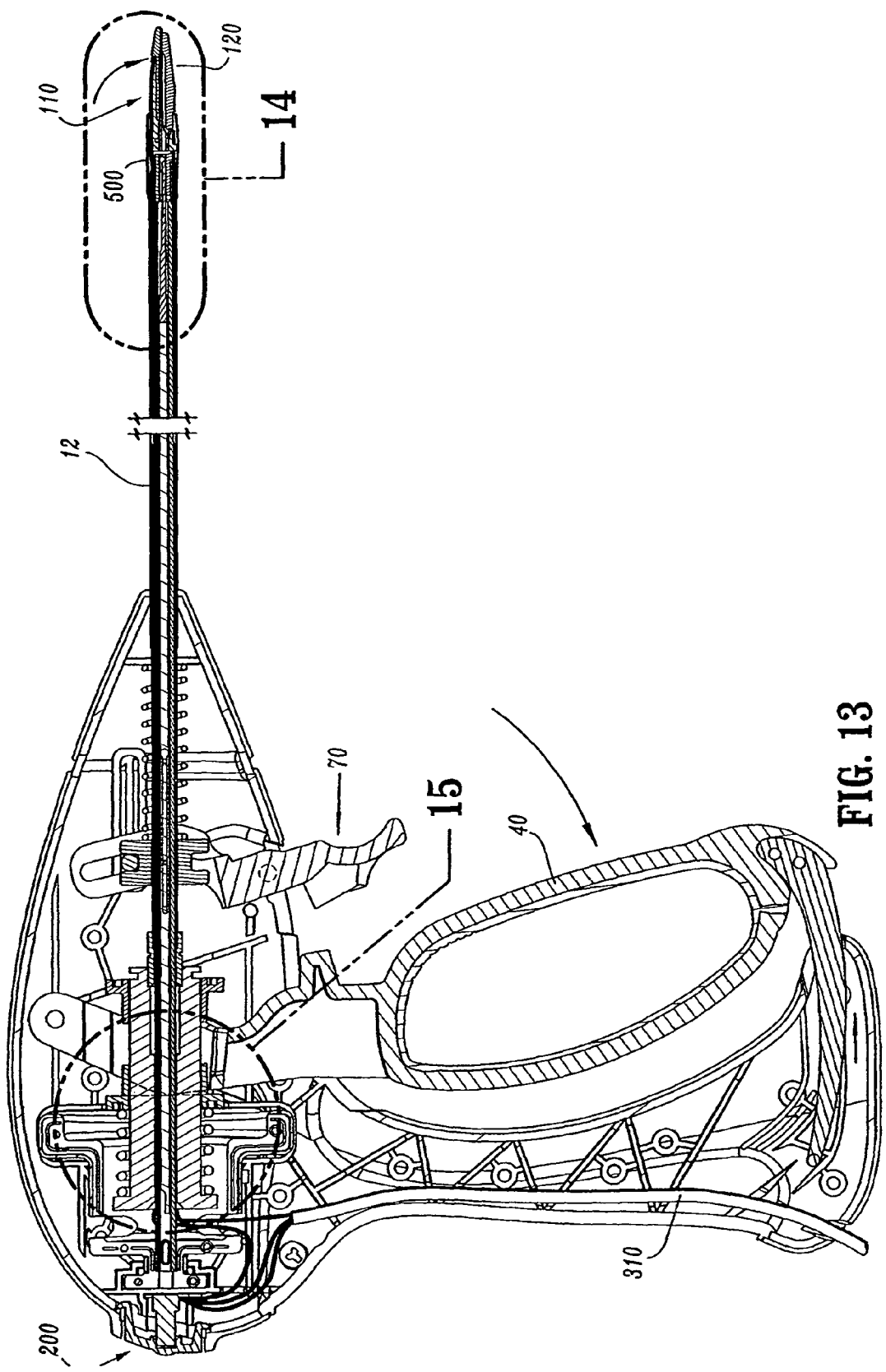
FIG. 13 is a side, cross section of the housing showing the moving components of the drive assembly during actuation and the end effector assembly.

In addition, the unilateral closure design of the end effector assembly 100 will also increase mechanical advantage. More particularly, as best shown in FIGS. 3 and 5, the unilateral end effector assembly 100 includes one stationary or fixed jaw member 120 that is mounted in fixed relation to the shaft 12 and a pivoting jaw member 110 mounted about a pivot pin 103 attached to the stationary jaw member 120. A reciprocating sleeve 60 is slidingly disposed within the shaft 12 and is remotely operable by the drive assembly 150 to move jaw member 110 relative to jaw member 120. The pivoting jaw member 110 includes a detent or protrusion 117 that extends from jaw member 110 through an aperture 62 disposed within the reciprocating sleeve 60 (FIG. 3). The pivoting jaw member 110 is actuated by sliding the sleeve 60 axially within the shaft 12 such that a distal end 63 of the aperture 62 abuts against the detent 117 on the pivoting jaw member 110 (See FIG. 3). Pulling the sleeve 60 proximally closes the jaw members 110 and 120 about tissue grasped therebetween and pushing the sleeve 60 distally opens the jaw members 110 and 120 for grasping purposes.

As best illustrated in FIGS. 3-9 and 18, a knife channel 115a and 115b runs through the center of the jaw members 110 and 120, respectively, such that a blade 185 from the knife assembly 140 can cut the tissue 420 grasped between the jaw members 110 and 120 when the jaw members 110 and 120 are in a closed position. More particularly, the blade 185 can only be advanced through the tissue 420 when the jaw members 110 and 120 are closed, thus preventing accidental or premature activation of the blade 185 through the tissue 420. The unilateral end effector assembly 100 is structured such that electrical energy can be routed through the sleeve 60 at the protrusion 117 contact point with the sleeve 60 or using a "brush" or lever (not shown) to contact the back of the moving jaw member 110 when the jaw member 110 closes. In this instance, the electrical energy would be routed through the protrusion 117 to the stationary jaw member 120.

As best illustrated in FIG. 2, jaw member 110 also includes a jaw housing 116 that has an insulative substrate or insulator 114 and an electrically conductive surface 112. Details relating to the specific structure of the jaw members 110 and 120 are disclosed in previously mentioned commonly owned U.S. patent application Ser. No. 10/460,926.

Figure 16:
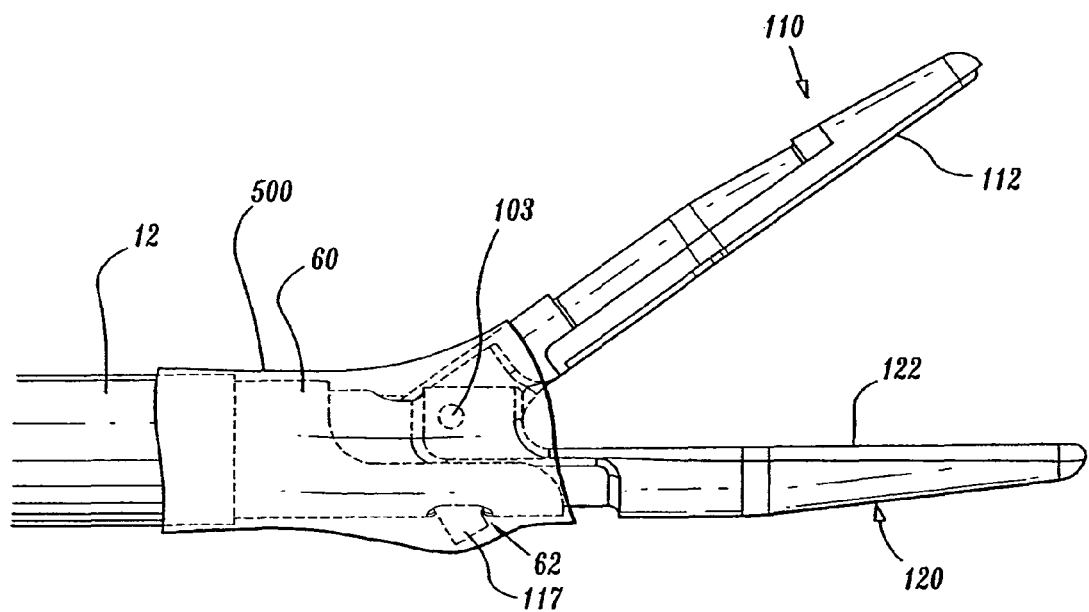
FIG. 16 is an enlarged, side view of the end effector assembly shown in an open configuration and having the insulating boot of the present disclosure.

As best shown in FIGS. 3 and 16, jaw member 110 includes a pivot flange 118 that, in turn, includes protrusion 117 that extends from pivot flange 118 and has an arcuately-shaped inner surface 111 dimensioned to matingly engage the aperture 62 of sleeve 60 upon retraction thereof. Pivot flange 118 also includes a pin slot 119 that is dimensioned to engage pivot pin 103 to allow jaw member 110 to rotate relative to jaw member 120 upon retraction of the reciprocating sleeve 60.

As explained in more detail below, pivot pin 103 mounts to the stationary jaw member 120 through a pair of apertures 101a and 101b disposed within a proximal portion of the jaw member 120. The pivot pin 103 serves as a common joint between the jaw members 110 and 120.

Jaw member 120 is designed to be fixed to the end of a rotating tube 160 that is part of the rotating assembly 80 such that rotation of the tube 160 around axis "B" of FIG. 1 will impart rotation to the end effector assembly 100 (See FIGS. 1, 2 and 15). Details relating to the rotation of the jaw members 110 and 120 are described in the previously mentioned commonly owned U.S. patent application Ser. No. 10/460,926, now U.S. Pat. No. 7,156,846, that is incorporated by reference herein in its entirety.

Fixed jaw member 120 is connected to a second electrical potential through tube 160 that is connected at its proximal end to lead 310c. More particularly, as best shown in FIGS. 2, 4, 10 and 11, fixed jaw 120 is welded to the rotating tube 160 and includes a fuse clip, spring clip or other electro-mechanical connection that provides electrical continuity to the fixed jaw member 120 from lead 310c. The rotating tube 160 includes an elongated guide slot 167 disposed in an upper portion thereof that is dimensioned to carry lead 311 therealong. Lead 311 carries a first electrical potential to movable jaw 110. A second electrical connection from lead 310c is conducted through the tube 160 to the fixed jaw member 120. Details relating to the electrical connections are described in the aforementioned U.S. patent application Ser. No. 10/460,926, now U.S. Pat. No. 7,156,846.

A tubular insulating boot 500 is included that is configured to mount over the pivot 103 and at least a portion of the end effector assembly 100. The tubular insulating boot 500 is flexible to permit opening and closing of the jaw members 110 and 120 about pivot 103. The flexible insulating boot 500 is made typically of any type of visco-elastic, elastomeric or flexible material that is biocompatible. Such a visco-elastic, elastomeric or flexible material is preferably durable and is configured to minimally impede movement of the jaw members 110 and 120 from the open to the closed positions. The particularly selected material of the flexible insulating boot 500 has a dielectric strength sufficient to withstand the voltages encountered during electrosurgery, and is suitable for use with a sterilization process that does not substantially impair structural integrity of the boot, such as an ethylene oxide process that does not melt or otherwise impair the structural integrity of the insulating boot 500. The insulating boot 500 is dimensioned to further reduce stray electrical potentials so as to reduce the possibility of subjecting the patient tissue to unintentional electrosurgical RF energy.

As best shown in FIGS. 2, 3, 12, 16 and 17, one end of the tubular insulating boot 500 is disposed on at least a portion of the exterior surface of shaft 12 while the other end of the tubular insulating boot 500 is disposed on at least a portion of the exterior surfaces of jaw members 110 and 120. Operability of the jaw members 110 and 120 is substantially unimpeded and not affected significantly by the flexible insulating boot 500. More particularly, the tubular insulating boot 500 is maintained on the shaft 12 such that boot 500 remains in a substantially stationary position axially with respect to reciprocating sleeve 60 and the jaw members 110 and 120. The flexible insulating boot 500 expands and contracts both radially and axially to cover the pivot pin 103 and to accommodate motion of the protrusion 117 and the movable jaw member 110.

Again, as previously mentioned, since one end of the tubular insulating boot 500 is disposed on at least a portion of the shaft 12 while the other end of the tubular insulating boot 500 is disposed on at least a portion of the exterior surfaces of fixed jaw member 120 and pivoting jaw member 110, operability of the pivoting jaw member 110 and the fixed jaw member 120, either with respect to reciprocation of the reciprocating sleeve 60 or rotation of the rotating tube 160, is not significantly limited by or impeded by the flexible insulating boot 500. The tubular insulating boot 500 does not interface with the shaft 12 but rather remains in a substantially stationary position axially with respect to reciprocating sleeve 60 and the jaw members 110 and 120.

As best shown in FIGS. 1, 4 and 10, once actuated, handle 40 moves in a generally arcuate fashion towards fixed handle 50 about the pivot pins 29a and 29b that forces driving flange 47 proximally against the drive assembly 150 that, in turn, pulls reciprocating sleeve 60 in a generally proximal direction to close jaw member 110 relative to jaw member 120. Moreover, proximal rotation of the handle 40 causes the locking flange 44 to release, i.e., "unlock", the trigger assembly 70 for selective actuation.

The operating features and relative movements of the internal working components of the forceps 10 and the trigger assembly 70 are shown by phantom representation in the various figures and explained in more detail with respect to the aforementioned U.S. patent application Ser. No. 10/460, 926, now U.S. Pat. No. 7,156,846, and also in U.S. patent application Ser. No. 10/970,307, now U.S. Pat. No. 7,232, 440, the contents of both of which are incorporated herein in their entirety.

As can be appreciated, as illustrated in FIG. 15, the utilization of an over-the-center pivoting mechanism will enable the user to selectively compress the coil spring 67 a specific distance that, in turn, imparts a specific pulling load on the reciprocating sleeve 60 that is converted to a rotational torque about the jaw pivot pin 103. As a result, a specific closure force can be transmitted to the opposing jaw members 110 and 120. The combination of the mechanical advantage of the over-the-center pivot along with the compressive force associated with the compression spring 67 facilitate and assure consistent, uniform and accurate closure pressure about tissue within a desired working pressure range of about 3 kg/cm$^2$ to about 16 kg/cm$^2$ and, preferably, about 7 kg/cm$^2$ to about 13 kg/cm$^2$. By controlling the intensity, frequency and duration of the electrosurgical energy applied to the tissue, the user can seal tissue.

As best shown in FIGS. 4, 6-9 and 18, the knife assembly 140 includes an elongated rod 182 having a bifurcated distal end comprising prongs 182a and 182b that cooperate to receive a knife bar 184 therein. The knife assembly 180 also includes a proximal end 183 that is keyed to facilitate insertion into tube 160 of the rotating assembly 80. A knife wheel 148 is secured to the knife bar 182 by a pin 143. More particularly, the elongated knife rod 182 includes apertures 181a and 181b that are dimensioned to receive and secure the knife wheel 148 to the knife rod 182 such that longitudinal reciprocation of the knife wheel 148, in turn, moves the elongated knife rod 182 to sever tissue 420. More details relating to the operational features of the knife assembly 180 are discussed in the previously mentioned U.S. patent application Ser. No. 10/460,926, which is incorporated herein by reference in its entirety.

As best shown in the exploded view of FIG. 4 and in FIGS. 14-15, the electrical leads 310a, 310b, 310c and 311 are fed through the housing 20 by electrosurgical cable 310. More particularly, the electrosurgical cable 310 is fed into the bottom of the housing 20 through fixed handle 50. Lead 310c extends directly from cable 310 into the rotating assembly 80 and connects (via a fused clip or spring clip or the like) to tube 60 to conduct the second electrical potential to fixed jaw member 120. Leads 310a and 310b extend from cable 310 and connect to the hand switch or joy-stick-like toggle switch 200. Details relating to the switch 200 are disclosed in the aforementioned U.S. patent application Ser. Nos. 10/460,926 and 10/970,307, now U.S. Pat. Nos. 7,156,846 and 7,232,440, respectively.

The jaw members 110 and 120 are electrically isolated from one another such that electrosurgical energy can be effectively transferred through the tissue to form seal 450, as shown in FIGS. 18 and 19. The two electrical potentials are isolated from one another by virtue of the insulative sheathing surrounding cable lead 311. At least one of the jaw members 110 and 120 is adapted to connect to a source of electrosurgical energy (a generator (not shown)) such that at least one of the jaw members 110 and 120 is capable of conducting electrosurgical energy to tissue held therebetween.

In addition, by virtue of the flexible insulating boot 500 of the present disclosure, desired motion of and force between the jaw members 110 and 120 is maintained and substantially unimpeded while at the same time insulating boot 500 further insulates the patient tissue from possible stray energy from the exterior surfaces of the jaw members 110 and 120 and the associated elements, e.g., pivot 103 (See FIG. 2). Details relating to various forceps that may be utilized with an insulating boot include the commonly-owned aforementioned instrument described in U.S. patent application Ser. Nos. 10/460,926 and 10/970,307, now U.S. Pat. Nos. 7,156,846 and 7,232,440, respectively, and commonly-owned and concurrently filed U.S. Provisional Patent Application Ser. No. 60/722,177 entitled "INLINE VESSEL SEALER AND DIVIDER", filed on Sep. 30, 2005, filed as U.S. patent application Ser. No. 11/540,335, published as U.S. Patent Application Publication No. US2007/0078456 A1, the entire contents of which is incorporated by reference herein.

As mentioned above with respect to FIG. 3, at least one jaw member, e.g., 120, may include a stop member 750 that limits the movement of the two opposing jaw members 110 and 120 relative to one another. The stop member 750 extends from the sealing surface 122 a predetermined distance according to the specific material properties (e.g., compressive strength, thermal expansion, etc.) to yield a consistent and accurate gap distance "G" (preferably between about 0.001 inches to about 0.006 inches, i.e., between about 0.03 mm to about 0.15 mm) during sealing (FIG. 18). The non-conductive stop members 750 are sprayed or otherwise deposited onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 750.

Figure 17:
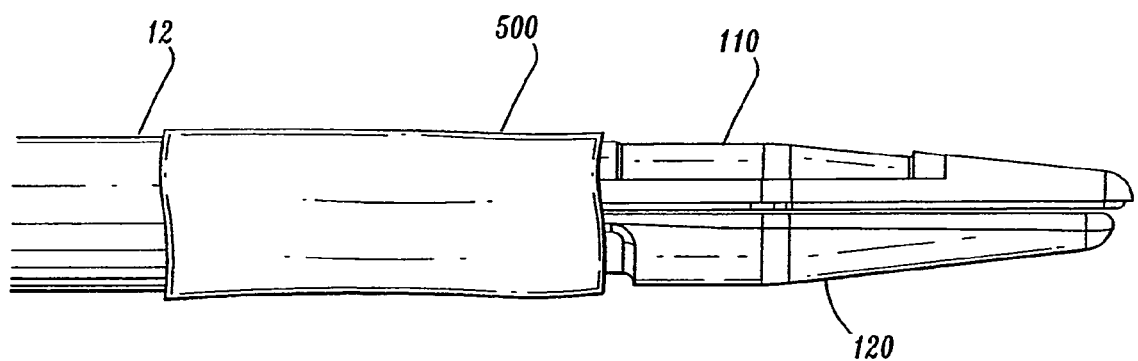
FIG. 17 is a side view of the end effector assembly shown in a closed configuration and having the insulating boot of the present disclosure with the jaw members in the closed position.

As best shown in FIGS. 4, 6-9, and 18-19, as energy is being selectively transferred to the end effector assembly 100, across the jaw members 110 and 120 and through the tissue 420, a tissue seal 450 forms isolating two tissue halves 420a and 420b. The knife assembly 140 is then activated via the trigger assembly 70, to progressively and selectively divide the tissue 420 along an ideal tissue plane in precise manner to effectively and reliably divide the tissue 420 into two sealed halves 420a and 420b (See FIGS. 18-19) with a tissue gap 475 therebetween. The knife assembly 140 allows the user to quickly separate the tissue 420 immediately after sealing or, if desired, without sealing, without substituting a cutting instrument through a cannula or trocar port. As can be appreciated, accurate sealing and dividing of tissue 420 is accomplished with the same forceps 10. Again, desired motion or movement of and force between the jaw members 110 and 120 is maintained and substantially unimpeded in the presence of the flexible insulating boot 500 of the present disclosure. For example, FIG. 16 is a side view of the end effector assembly 100 having the flexible insulating boot 500 of the present disclosure illustrating the jaw members 110 and 120 in the open position. FIG. 17 is a side view of the end effector assembly 100 having the flexible insulating boot 500 of the present disclosure illustrating the jaw members 110 and 120 in the closed position.

Figure 20:
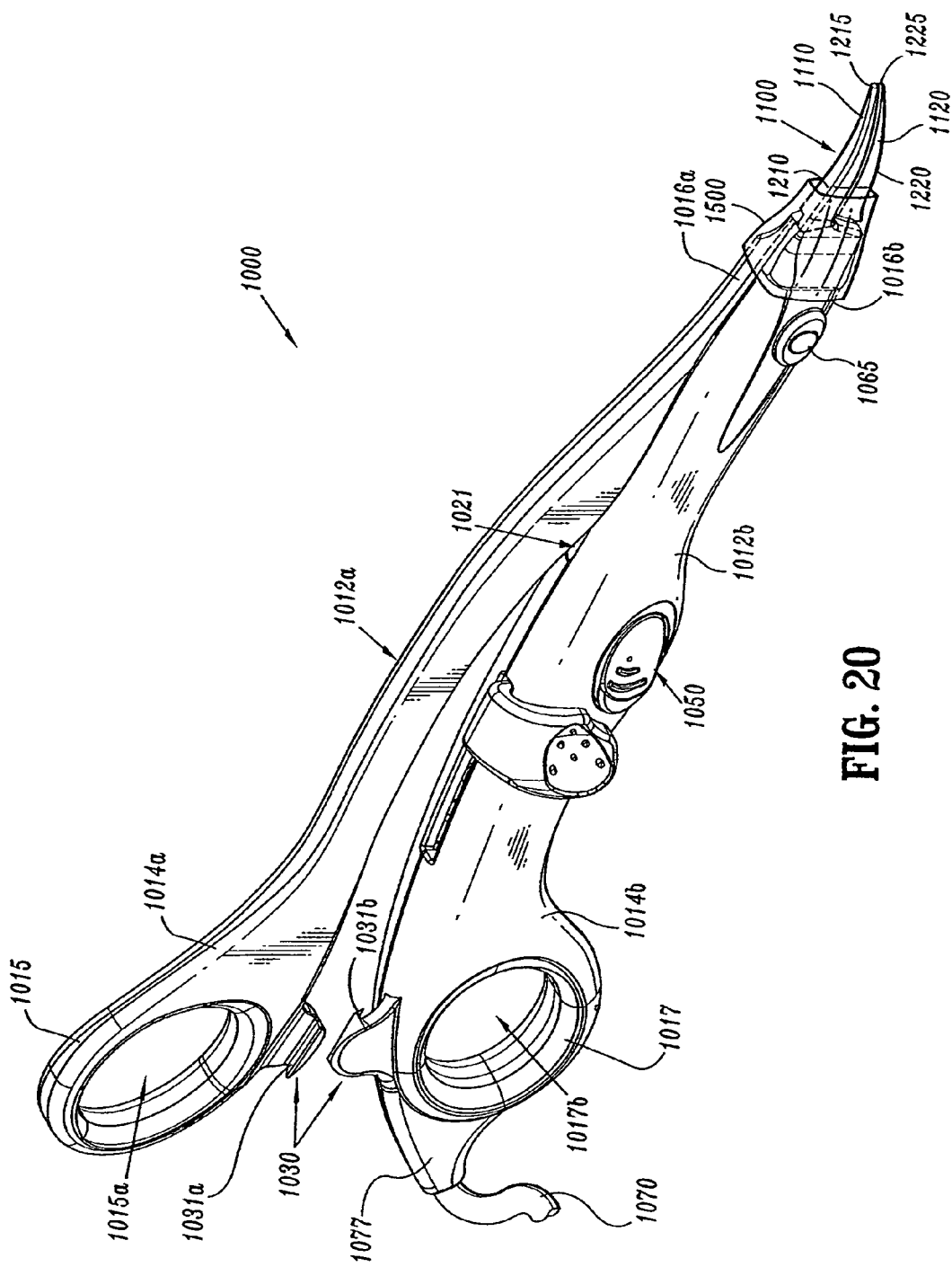
FIG. 20 is a left, front perspective view of an open forceps with a cutting mechanism having an insulating boot according to the present disclosure.
Figure 21:
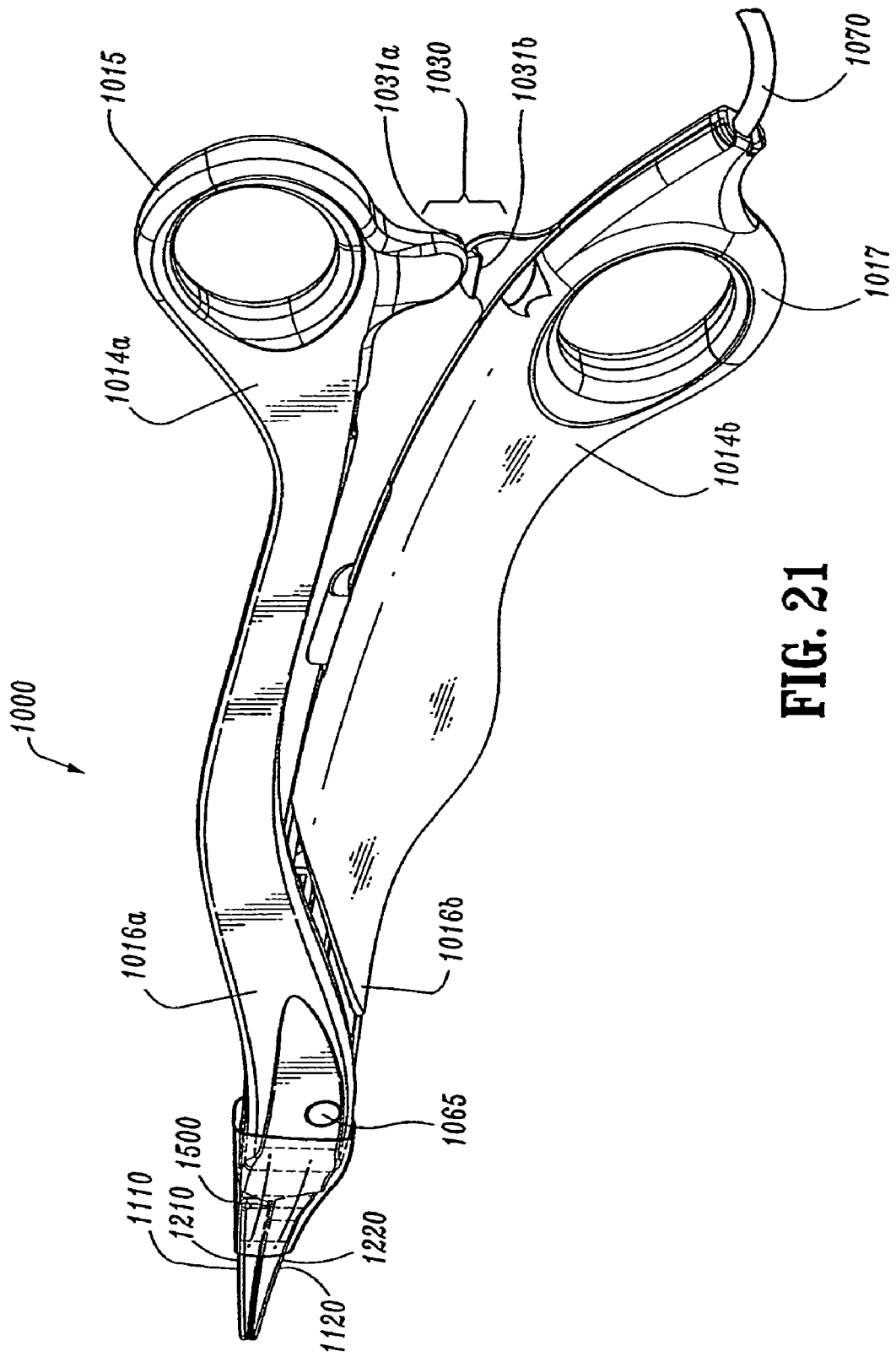
FIG. 21 is a right, rear perspective view of the forceps of FIG. 20.

FIGS. 20 and 21 show an open forceps 1000 for use with an insulating boot 1500 of the present disclosure. Forceps 1000 includes elongated shaft portions 1012a and 1012b each having a proximal end 1014a, 1014b and a distal end 1016a and 1016b, respectively. The forceps 1000 includes an end effector assembly 1100 that attaches to the distal ends 1016a and 1016b of shafts 1012a and 1012b, respectively. The end effector assembly 1100 includes pair of opposing jaw members 1110 and 1120 that are pivotably connected about a pivot pin 1065 and that are movable relative to one another to grasp vessels and/or tissue.

Each shaft 1012a and 1012b includes a handle 1015 and 1017, respectively, disposed at the proximal end 1014a and 1014b thereof that each define a finger hole 1015a and 1017b, respectively, therethrough for receiving a finger of the user. Finger holes 1015a and 1017b facilitate movement of the shafts 1012a and 1012b relative to one another that, in turn, pivot the jaw members 1110 and 1120 from an open position wherein the jaw members 1110 and 1120 are disposed in spaced relation relative to one another to a clamping or closed position wherein the jaw members 1110 and 1120 cooperate to grasp tissue or vessels therebetween.

Shaft 1012a is secured about pivot 1065 and positioned within a cut-out or relief 1021 such that shaft 1012a is movable relative to shaft 1012b. More particularly, when the user moves the shaft 1012a relative to shaft 1012b to close or open the jaw members 1110 and 1120, the distal portion of shaft 1012a moves within cutout 1021. One of the shafts, e.g., 1012b, includes a proximal shaft connector 1077 that is designed to connect the forceps 1000 to a source of electrosurgical energy such as an electrosurgical generator (not shown).

Figure 22:
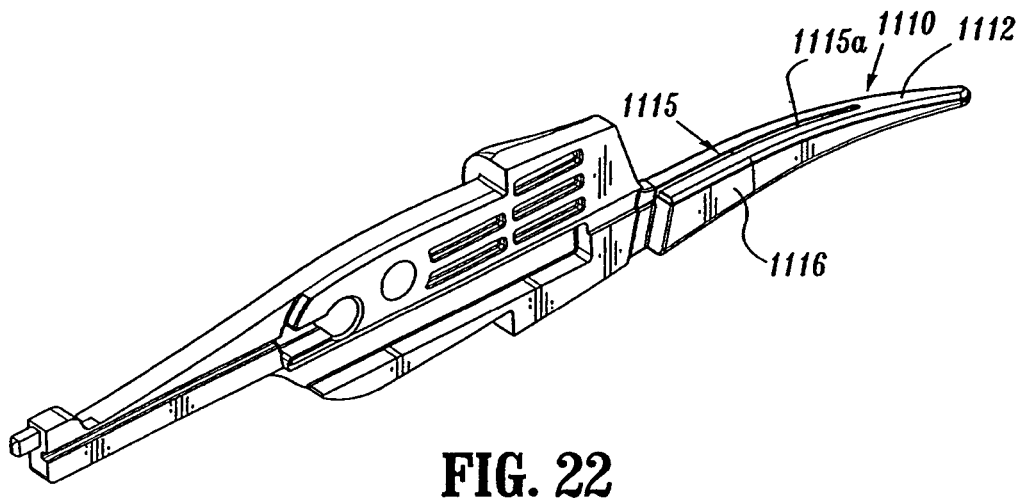
FIG. 22 is an enlarged, left perspective view of one of the jaw members of the forceps of FIG. 20.
Figure 23:
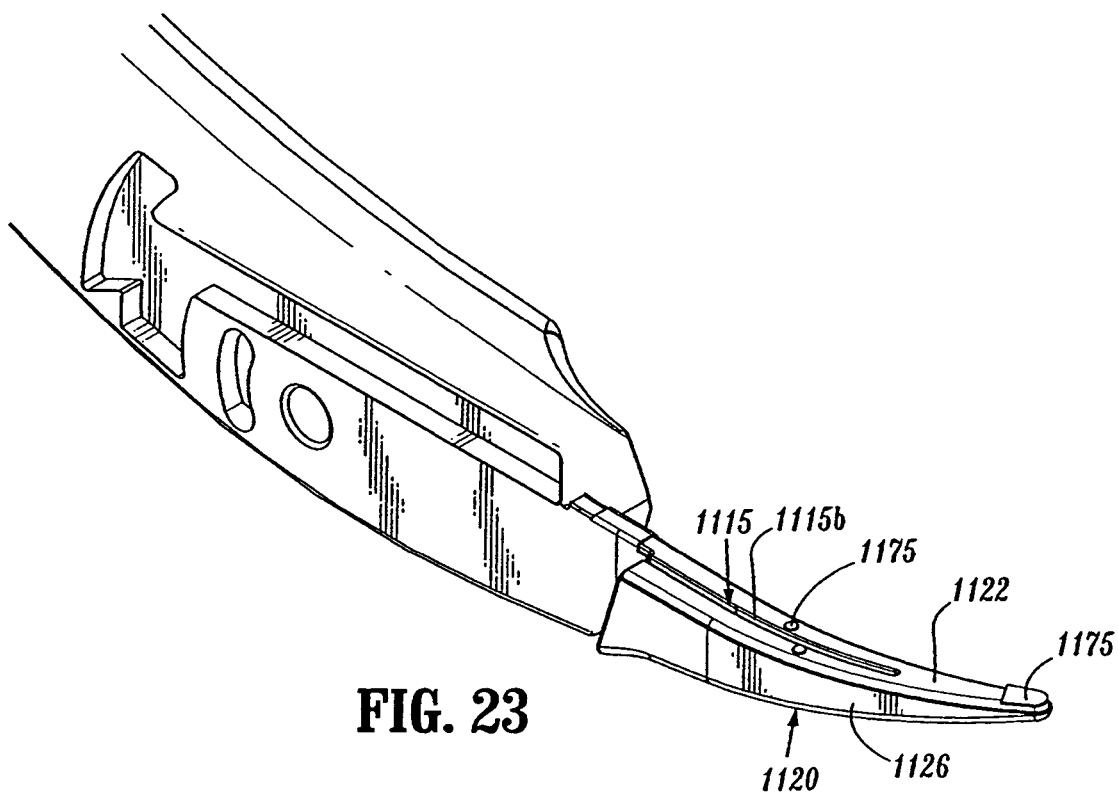
FIG. 23 is an enlarged, perspective view of the other jaw member of the forceps of FIG. 20.
Figure 25:
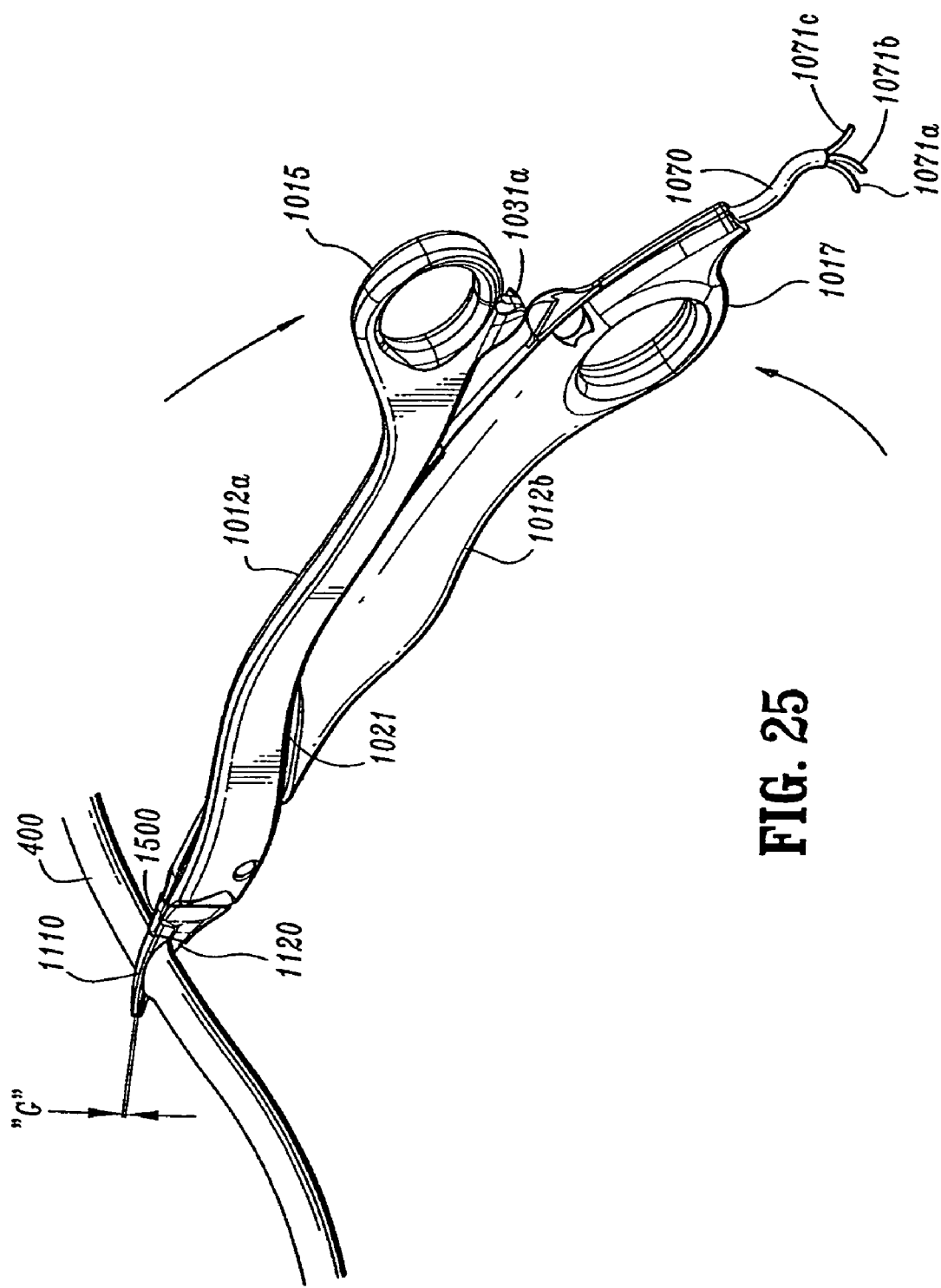
FIG. 25 is a rear, perspective view of the forceps of FIG. 20 shown grasping tissue with a ratchet mechanism shown prior to engagement.
Figure 26:
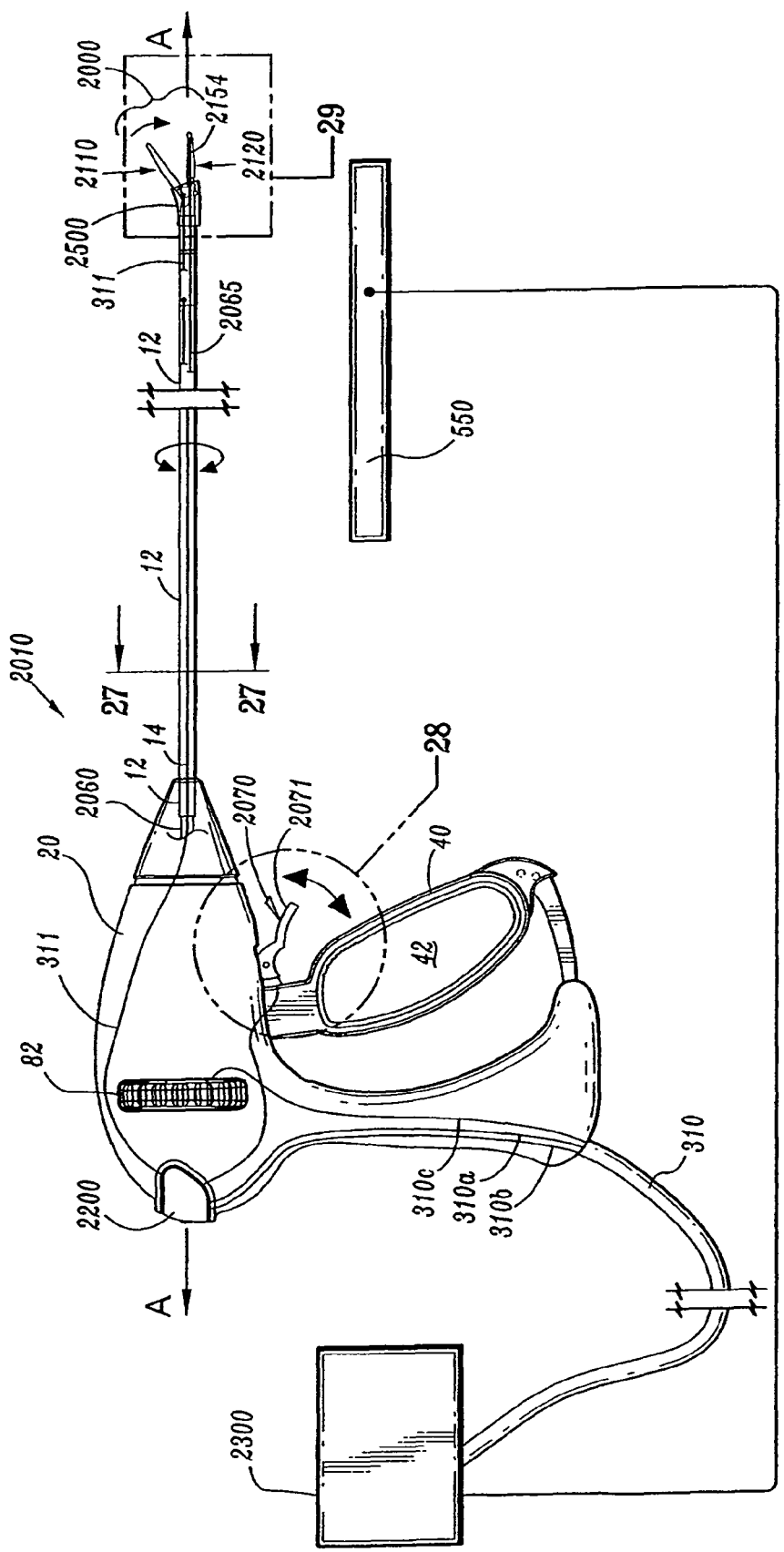
FIG. 26 is a side view of an endoscopic forceps showing a housing, a shaft, an end effector assembly having an insulating boot according to the present disclosure and a trigger assembly in a first position.
Figure 30:
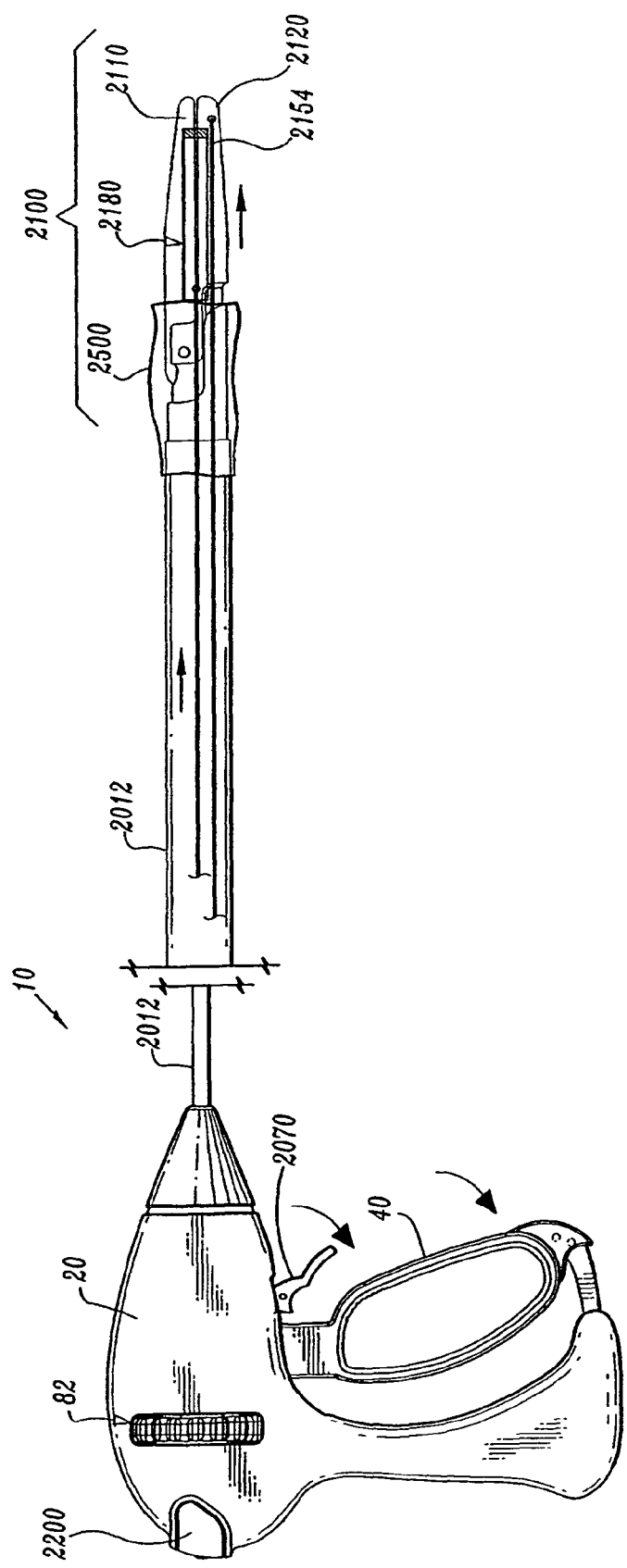
FIG. 30 is a side view of the trigger assembly in a second position for advancing a knife within the end effector assembly and having the insulating boot according to the present disclosure.

The distal end of the cable 1070 connects to a handswitch 1050 to permit the user to selectively apply electrosurgical energy as needed to seal tissue or vessels grasped between jaw members 1110 and 1120 (See FIGS. 20, 21 and 25). As best shown in FIGS. 22-23, jaw members 1110 and 1120 include outer insulative coatings or layers 1116 and 1126 that are dimensioned to surround the outer periphery of jaw member 1110 and 1120 and expose electrically conductive sealing surfaces 1112 and 1122, respectively on an inner facing surface thereof. The electrically conducive sealing surfaces 1112 and 1122 conduct electrosurgical energy to the tissue upon activation of the handswitch 1050 such that the two opposing electrically conductive sealing surfaces 1112 and 1122 conduct bipolar energy to seal tissue disposed between the sealing surfaces 1112 and 1122 upon activation. At least one of the jaw members 1110 and 1120 is adapted to connect to the source of electrosurgical energy (not shown) such that at least one of the jaw members 1110 and 1120 is capable of conducting electrosurgical energy to tissue held therebetween.

Figure 24:
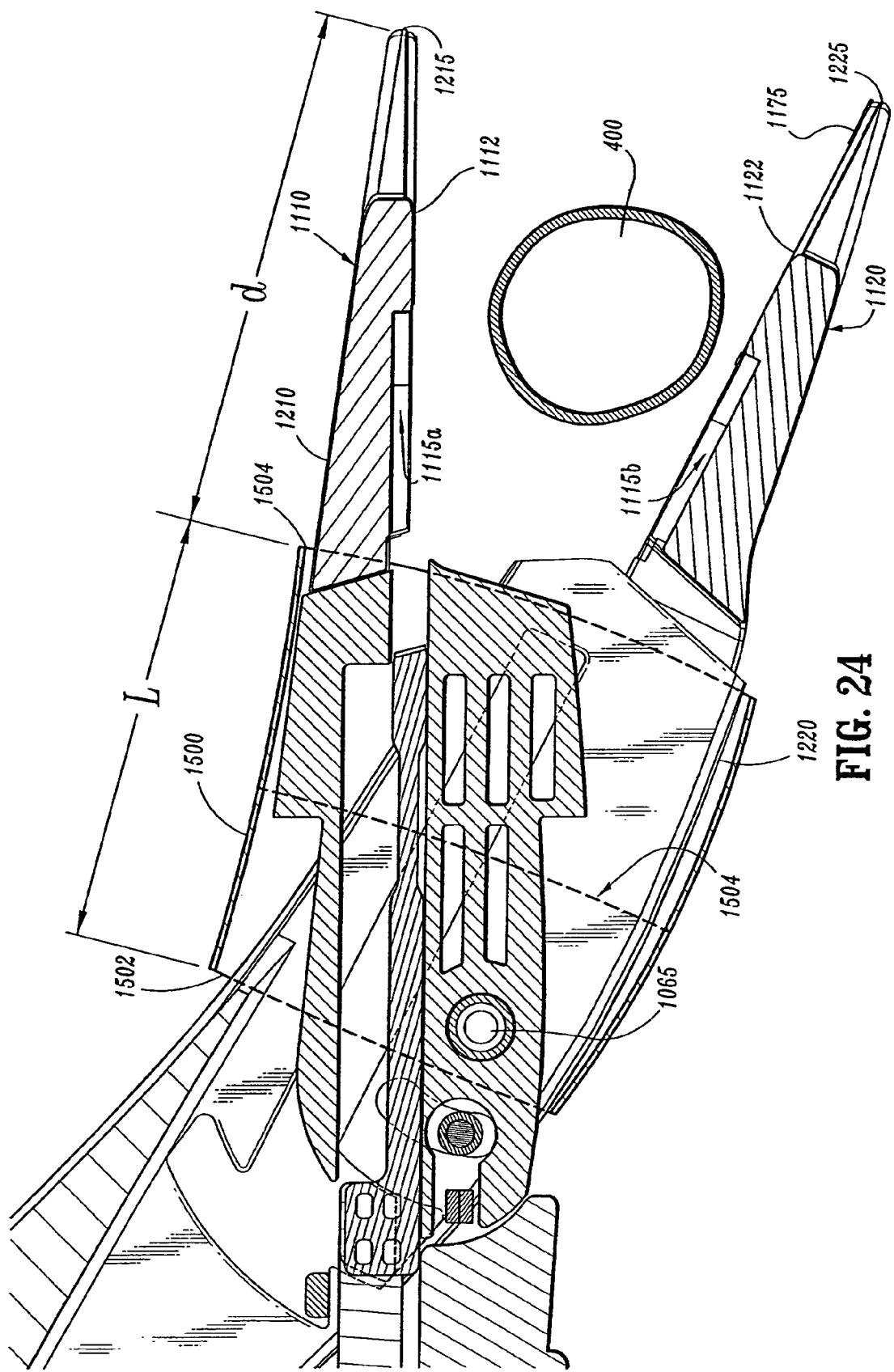
FIG. 24 is a side cross sectional view showing the forceps of FIG. 20 in open configuration for grasping tissue.

As best shown in FIG. 24, the upper jaw member 1110 includes an exterior surface or outer edge 1210 extending from a distal end or tip 1215 of the upper jaw member 1110. Similarly, the lower jaw member 1120 includes an exterior surface or outer edge 1220 extending from a distal end or tip 1225 of the lower jaw member 1120. In addition, in accordance with the present disclosure, generally tubular insulating boot 1500 having a length "L" may be positioned about at least a portion of the end effector assembly 1100. The distal end 1504 of the insulating boot 1500 is disposed on the outer edge 1210 of the upper jaw member 1110 at a distance "d" retracted away from the tip 1215 and at a corresponding position on the outer edge 1220 of the lower jaw member 1120 retracted away from the tip 1225.

In one embodiment, the length "L" of the insulating boot 1500 is such that the proximal end 1502 of the insulating boot 1500 is disposed on the outer edges 1210 and 1220 so that the pivot pin 1065 remains exposed. In an alternate embodiment shown in phantom in FIG. 24, the length "L" of the insulating boot 1500 is such that the proximal end 1502 of the insulating boot 1500 is disposed on the outer edges 1210 and 1220 so that the pivot pin 1065 is covered by the insulating boot 1500. Those skilled in the art recognize that the distance "d" and the length "L" of the insulating boot 1500 are chosen so as to maximize continued operability of the jaw members 1110 and 1120 to perform their intended functions.

In either embodiment, the insulating boot 1500 limits stray current dissipation to surrounding tissue upon activation and continued use of the forceps 1000. As mentioned above, the insulating boot 1500 is made from any type of visco-elastic, elastomeric or flexible material that is biocompatible and that is configured to minimally impede movement of the jaw members 1110 and 1120 from the open to closed positions. Moreover, in one embodiment, the material is selected to have a dielectric strength sufficient to withstand the voltages encountered during electrosurgery, and is suitable for use with a sterilization process that does not substantially impair structural integrity of the boot, such as an ethylene oxide process. More particularly, the insulating boot 1500 further reduces stray electrical potential so as to reduce the possibility of subjecting the patient tissue to unintentional electrosurgical RF energy.

As best shown in FIG. 24, the tubular insulating boot 1500 is disposed on at least a portion of the exterior surface 1210 of jaw members 1110 and 1120 such that operability of the jaw members 1110 and 1120 is substantially unimpeded and not affected significantly by the flexible insulating boot 1500. More particularly, the tubular insulating boot 1500 remains in a substantially stationary position axially with respect to the jaw members 1110 and 1120, i.e., the distance "d" remains substantially constant during motion of the upper jaw member 1110 with respect to the lower jaw member 1120. However, the flexible insulating boot 1500 expands and contracts both radially and axially to accommodate motion of the movable jaw member 1110, and to cover the pivot pin 1103 where applicable.

Details relating to the jaw members 1110 and 1120 and various elements associated therewith are discussed in commonly-owned U.S. application Ser. No. 10/962,116, filed on Oct. 8, 2004, and entitled "Open Vessel Sealing Instrument with Hourglass Cutting Mechanism and Over-Ratchet Safety", the entire contents of which are hereby incorporated by reference herein.

As best illustrated in FIG. 23, jaw member 1120 (or jaw member 1110) includes one or more stop members 1175 disposed on the inner facing surface of the electrically conductive sealing surface 1122. The stop members are designed to facilitate gripping and manipulation of tissue and to define a gap "G" between opposing sealing surfaces 1112 and 1122 during sealing (See FIGS. 24 and 25). The separation distance during sealing or the gap distance "G" is within the range of about 0.001 inches (about 0.03 millimeters) to about 0.006 inches (about 0.016 millimeters) for optimizing the vessel sealing process.

As best seen in FIGS. 22 and 23, the jaw members 1110 and 1120 include a knife channel 1115 disposed therebetween that is configured to allow distal translation of a cutting mechanism (not shown) therewithin to sever tissue disposed between the seal surfaces 1112 and 1122. The complete knife channel 1115 is formed when two opposing channel halves 1115a and 1115b associated with respective jaw members 1110 and 1120 come together upon grasping of the tissue. Details relating to the cutting mechanism and associated actuating mechanism (not shown) are discussed in commonly-owned U.S. application Ser. No. 10/962,116, the entire contents of which are hereby incorporated by reference herein.

FIG. 21 shows the details of a ratchet 1030 for selectively locking the jaw members 1110 and 1120 relative to one another during pivoting. A first ratchet interface 1031a extends from the proximal end 1014a of shaft member 1012a towards a second ratchet interface 1031b on the proximal end 1014b of shaft 1012b in general vertical registration therewith such that the inner facing surfaces of each ratchet 1031a and 1031b abut one another upon closure of the jaw members 1110 and 1120 about the tissue 400. The position associated with the cooperating ratchet interfaces 1031a and 1031b holds a specific, i.e., constant, strain energy in the shaft members 1012a and 1012b that, in turn, transmits a specific closing force to the jaw members 1110 and 1120 within a specified working range of about 3 kg/cm² to about 16 kg/cm² when the jaw members 1110 and 1120 are ratcheted.

In operation, the surgeon utilizes the two opposing handle members 1015 and 1017 to grasp tissue between jaw members 1110 and 1120. The surgeon then activates the handswitch 1050 to provide electrosurgical energy to each jaw member 1110 and 1120 to communicate energy through the tissue held therebetween to effect a tissue seal. Once sealed, the surgeon activates the actuating mechanism to advance the cutting blade through the tissue to sever the tissue 400 along the tissue seal.

The jaw members 1110 and 1120 are electrically isolated from one another such that electrosurgical energy can be effectively transferred through the tissue to form a tissue seal. Each jaw member, e.g., 1110, includes a uniquely-designed electrosurgical cable path disposed therethrough that transmits electrosurgical energy to the electrically conductive sealing surface 1112. The two electrical potentials are isolated from one another by virtue of the insulative sheathing surrounding each cable lead 1071a, 1071b and 1071c. In addition, to further enhance safety, as noted previously, insulating boot 1500 may be positioned about at least a portion of the end effector assembly 1000, and optionally the pivot 1065, to limit stray current dissipation to surrounding tissue upon activation and continued use of the forceps 1010. As mentioned above, the insulating boot 1500 is made from any type of visco-elastic, elastomeric or flexible material that is biocompatible and that is configured to minimally impede movement of the jaw members 1110 and 1120 from the open to closed positions.

Figure 34A:
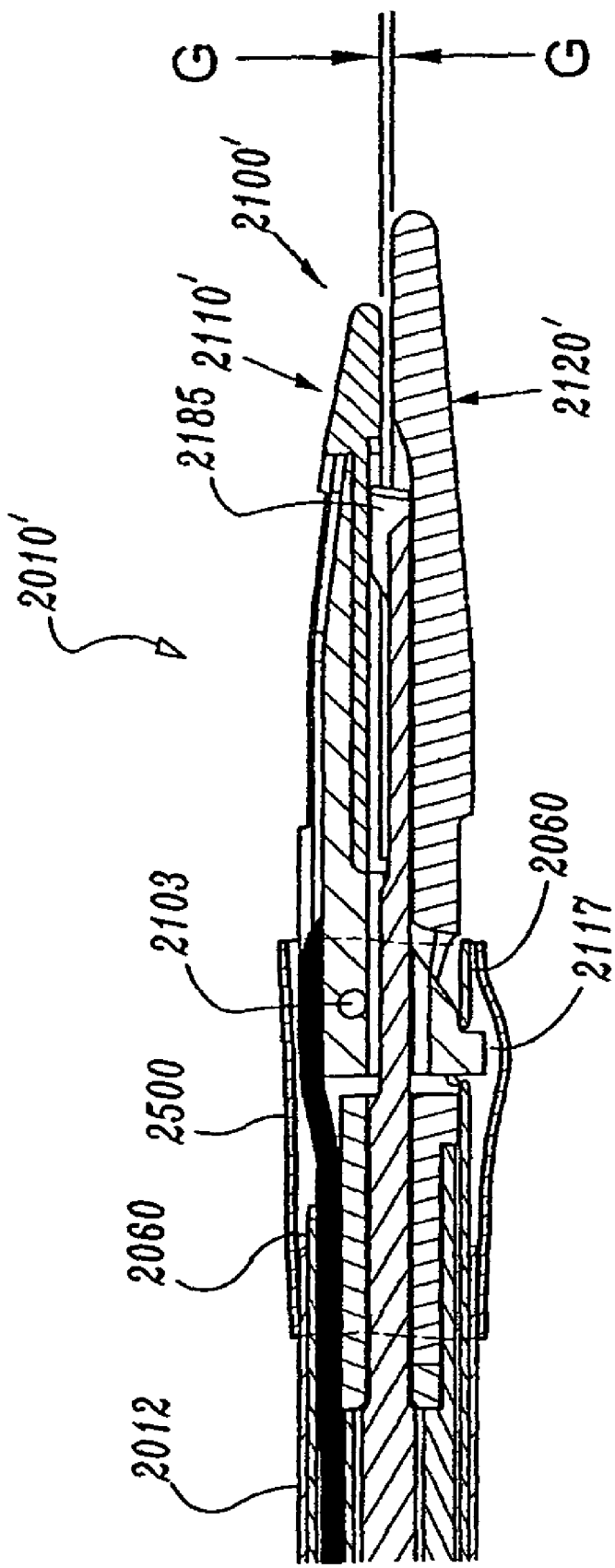
FIG. 34A is an enlarged, side schematic view of another embodiment of an end effector assembly having the insulating boot according to the present disclosure.

The presently disclosed insulating boot may also be utilized with a forceps 2010 designed for both bipolar electrosurgical treatment of tissue (either by vessel sealing as described above or coagulation or cauterization with other similar instruments) and monopolar treatment of tissue. For example, FIGS. 26-32 show one embodiment of a forceps 2010 that includes a monopolar element, e.g., element 2154 that may be selectively extended and selectively activated to treat tissue. FIGS. 33A-33B show alternate embodiments of the present disclosure that show that the knife 2185 may be extended from the distal end of the end effector assembly 2100 and selectively energized to treat tissue in a monopolar fashion. FIG. 34A shows another embodiment of a forceps 2010' wherein the bottom jaw member 2120' extends distally from the top jaw member 2110' to allow the surgeon to selectively energize the bottom jaw member 2120' and treat tissue in a monopolar fashion. FIG. 34B shows yet another embodiment of a forceps 2010" wherein the jaw members 2110" and 2120" include tapered distal ends that are selectively energized with a single electrical potential to treat tissue in a monopolar fashion. FIGS. 35A-38B show other configurations of the end effector assembly and/or bottom or second jaw member that are configured to suit a particular purpose or to achieve a desired surgical result. An insulating boot 2500 may be configured to cover the various uninsulated elements of the end effector assembly 1100 of the above mentioned and below further described elements including but not limited to portions of one or both of the jaw members 2110 and 2120, the pivot 2103 and the knife assembly 2180 etc. The insulating boot 2500 is contemplated to be particularly useful with forceps capable of monopolar activation since the boot prevents the various uninsulated elements from acting as alternative or unintended current sources or paths during activation that may result in unintended or undesirable tissue effects during a particular surgical procedure.

Figure 31:
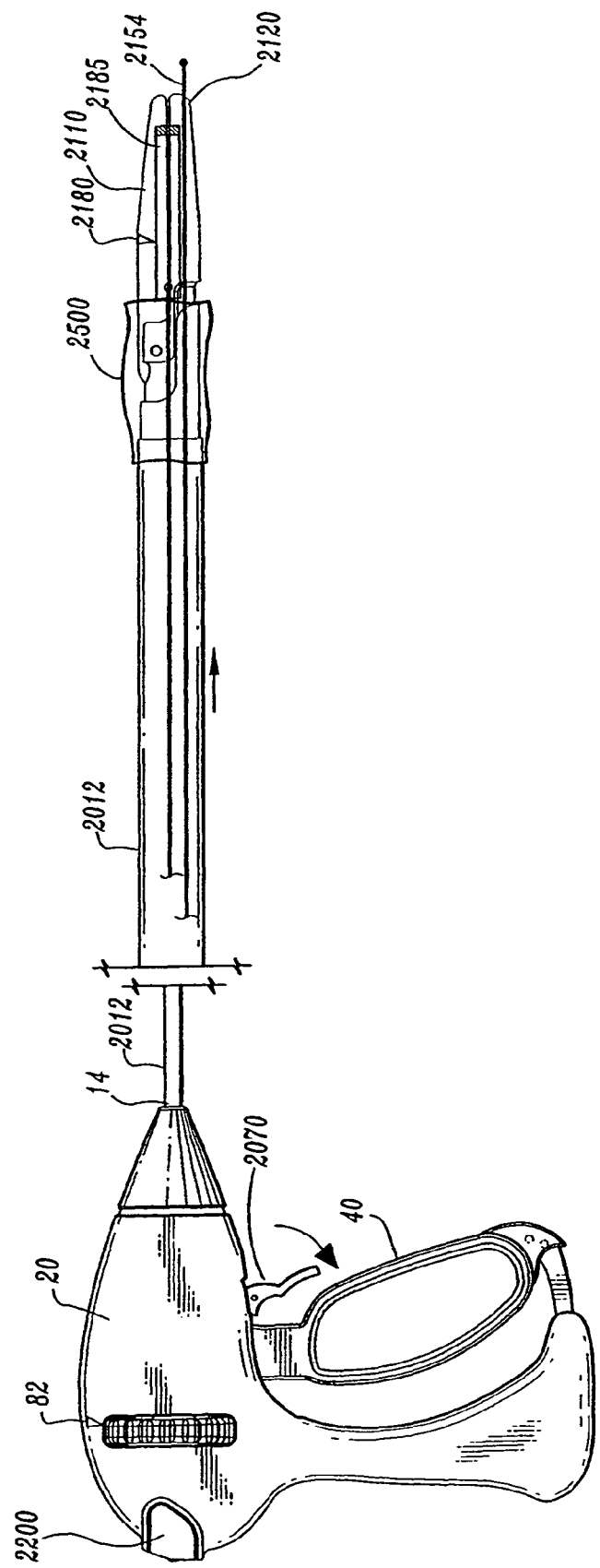
FIG. 31 is a side view of the trigger assembly in a third position for extending a monopolar element from a distal end of the end effector assembly.
Figure 32:
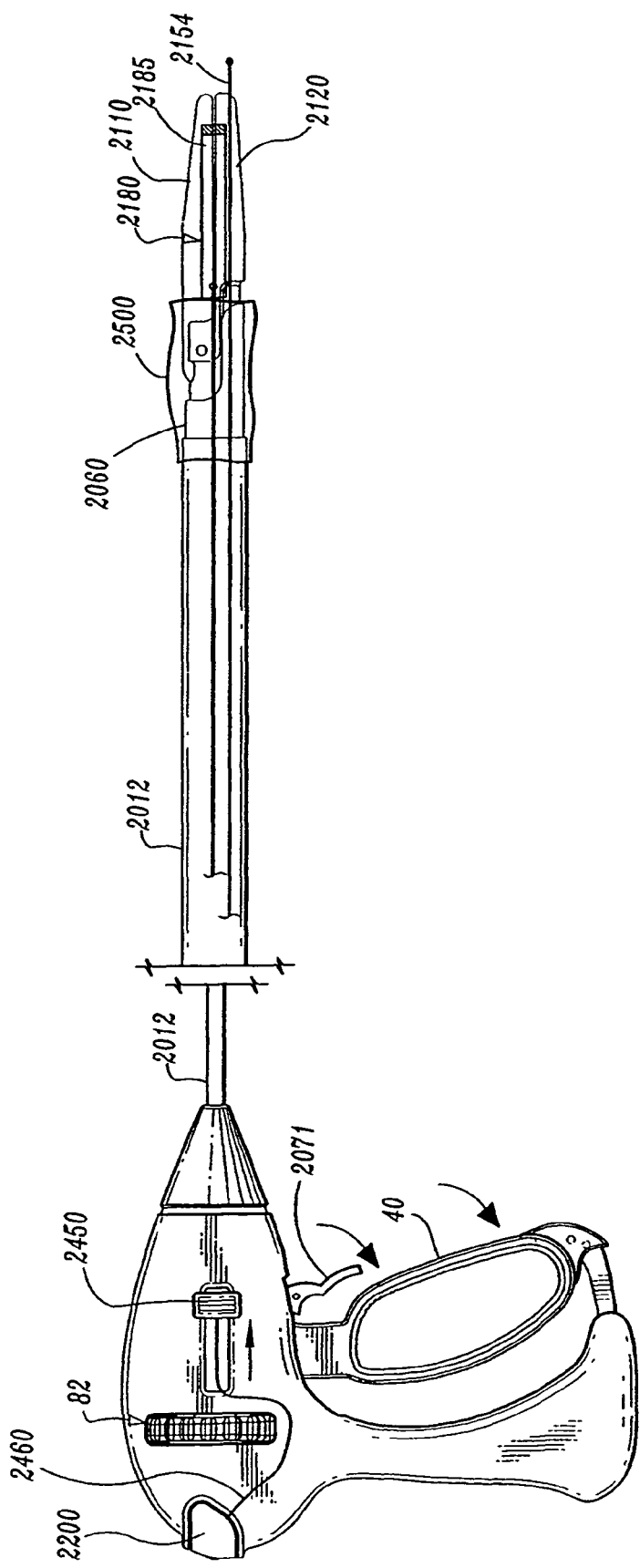
FIG. 32 is a side view of an alternate embodiment of the present invention showing a second actuator advancing the monopolar element relative to the distal end of the end effector.

More particularly, FIGS. 26-31 show one embodiment wherein a monopolar element 2154 is housed for selective extension within one jaw member, e.g., jaw member 2120, of the end effector assembly 2100. Monopolar element 2154 is designed to move independently from knife assembly 2180 and may be extended by further proximal movement of the trigger assembly 2070 (FIGS. 26, 30 and 31) or by a separate actuator 2450 (FIG. 32).

The monopolar element 2154 may be connected to a reciprocating rod 2065 that extends through an elongated notch 2013 in the outer periphery of the shaft 2012 as best seen in FIG. 27. Drive rod 2060 that actuates the knife 2185 extends through the inner periphery of shaft 2012. In order to extend the monopolar element 2154, the jaw members 2110 and 2120 are initially closed and the knife 2185 is advanced distally utilizing the trigger assembly 2070 (See FIG. 30). As best shown in FIG. 28, the trigger 2071 is initially advanced to translate the knife 2185 distally to cut through tissue, i.e., the "cut" stage (shown in phantom). Thereafter and as shown in FIGS. 28 and 31, the trigger 2071 may be further actuated in a proximal direction to extend the monopolar element 2154, i.e., the "extend" stage (shown in phantom).

As best shown in FIG. 29, a tubular insulating boot 2500 is included that is configured to mount over the pivot 2103, connecting the upper, pivoting jaw member 2110 with the lower, fixed jaw member 2120, and over at least a portion of the end effector assembly 2100. The tubular insulating boot 2500 is flexible to permit opening and closing of the jaw members 2110 and 2120 about the pivot 2103. The flexible insulating boot 2500 is made typically of any type of visco-elastic, elastomeric or flexible material that is biocompatible. More particularly, the insulating boot 2500 is configured to reduce stray electrical potential so as to reduce the possibility of subjecting the patient tissue to unintentional electrosurgical RF energy.

As best shown in FIG. 29, one end of the tubular insulating boot 2500 is disposed on at least a portion of the exterior surface of shaft 2012 while the other end of the tubular insulating boot 2500 is disposed on at least a portion of the exterior surfaces of fixed jaw member 2120 and pivoting jaw member 2110 such that operability of the jaw members 2110 and 2120 is substantially unimpeded and not affected significantly by the flexible insulating boot 2500. More particularly, the tubular insulating boot 2500 is maintained on the shaft 2012 such that boot 2500 remains in a substantially stationary position axially with respect to reciprocating sleeve 2060 and the jaw members 2110 and 2120. The flexible insulating boot 2500 expands and contracts both radially and axially to cover the pivot pin 2103 and to accommodate motion of protrusion 2117 and the movable jaw member 2110.

Details relating to this particular embodiment of a monopolar forceps is disclosed in aforementioned commonly-owned U.S. application Ser. No. 10/970,307, the entire contents of which are hereby incorporated by reference herein.

FIG. 32 shows another embodiment of the present disclosure wherein the monopolar element 2154 is selectively extendible utilizing a second actuator 2450. As described above, the knife 2185 is advanced by actuating the trigger 2071 in a generally proximal direction. The monopolar element 2154 is selectively advanceable independently of the knife 2185 and may be extended when the jaw members 2110 and 2120 are disposed in either the open configuration or closed configuration. The actuator 2450 may be electrically configured to activate the monopolar element 2154 automatically once extended or manually by activation switch 2200 or perhaps another switch (not shown). As mentioned above, a safety circuit 2460 may be employed to deactivate jaw members 2110 and 2120 when the monopolar element 2154 is extended such that activation of the switch 2200 energizes the monopolar element 2154. In the case of a separate activation switch for the monopolar element, the safety circuit would deactivate the switch 2200.

In a similar manner as discussed previously with respect to FIG. 29, and as shown in FIG. 32, the tubular insulating boot 2500 is included that is configured to mount over the pivot 2103 and at least a portion of the end effector assembly 2100. The tubular insulating boot 2500 is flexible to permit opening and closing of the jaw members 2110 and 2120 about pivot 2103.

Those skilled in the art recognize that the material properties of the insulating boot 2500 and operability considerations from disposition of the insulating boot 2500 are in all respects either similar to or in some cases identical to those described in the preceding discussion with respect to FIGS. 26-31.

FIGS. 33A-33C show another alternate embodiment of the present disclosure of a forceps 2200 wherein the knife 2185 can be extended distally beyond the jaw members 2210 and 2220, respectively, and separately energized to treat tissue. In this instance, when the knife is extended beyond the jaw members 2210 and 2220, respectively, the knife 2185 becomes the monopolar element.

As illustrated in FIGS. 33A-33C and partially in FIG. 34B, once the knife 2185 extends beyond the jaw members 2110 and 2120, a safety or switch deactivates energizing circuitry to the jaw members 2110 and 2120 and activates the energizing circuitry to the knife 285 such that activation of the switch 2200 energizes the knife 2185 and the jaw members remain neutral. For example, the stop 2119 may act as a safety switch such that upon being forced by the knife 2185 out of or away from the knife channel 2115, the stop 2119 deactivates circuitry to the jaw members 2210 and 2220 and activates circuitry to the monopolar knife 2185 and the return electrode 2550. A separate lead 2069 may be used to electrically communicate with the generator 2300 (See FIG. 34B). As can be appreciated, the knife 2185 may now be used in a monopolar fashion to treat tissue.

Upon release of a trigger such as trigger 2070 (See FIG. 26), the knife 2185 automatically retracts into the knife channel 2115 and back to the pre-actuated position as shown in FIG. 33A. At the same time, the stop 2119 reverts to its original position to temporarily block the knife channel 2115 for subsequent actuation.

Again, in a similar manner as discussed previously with respect to FIG. 29, the tubular insulating boot 2500 is included that is configured to mount over the pivot 2103 and at least a portion of the end effector assembly 2200. The tubular insulating boot 2500 is flexible to permit opening and closing of the jaw members 2210 and 2220 about pivot 2103.

Again, those skilled in the art recognize that the material properties of the insulating boot 2500 and operability considerations from disposition of the insulating boot 2500 are similar to those described in the preceding discussions.

As shown in FIG. 34A and partially in the schematic FIG. 34B, another embodiment of a forceps 2010' according to the present disclosure wherein the lower jaw member 2120' is designed to extend beyond the distal end of jaw member 2110'. In order to switch from a bipolar mode of the operation to a monopolar mode, the surgeon activates a switch or control that energizes jaw member 2120' to a first potential and activates a return pad 2550 to a second potential. Energy is transferred from jaw member 2120, through tissue, and to the return pad 2550 to treat tissue. The distal end of jaw member 2120' acts as the monopolar element for treating the tissue and may be shaped accordingly to enhance electrosurgical effect.

FIG. 34B shows yet another schematic embodiment of a forceps 2010" according to the present disclosure wherein the distal ends of both jaw members 2110" and 2120" are shaped to treat tissue when disposed in a monopolar mode. More particularly, the distal tips 2112a" and 2122a" are preferably elongated or tapered to enhance energy delivery when the forceps 2010" is disposed in the monopolar mode. When disposed in the bipolar mode, the tapered ends 2112a" and 2122a" do not effect treating tissue between electrically conductive plates 2112" and 2122".

A control switch 2505 is preferably included that regulates the transition between bipolar mode and monopolar mode. Control switch 2505 is connected to generator 2300 via cables 2360 and 2370. A series of leads 2510, 2520 and 2530 are connected to the jaw members 2110", 2120" and the return electrode 2550, respectively. As best shown in the table depicted in FIG. 34B, each lead 2510, 220, and 2530 is provided with an electrical potential or remains neutral depending upon the particular "mode" of the forceps 2010". For example, in the bipolar mode, lead 2510 (and, in turn, jaw member 2110") is energized with a first electrical potential and lead 2520 (and, in turn, jaw member 2120") is energized with second electrical potential. As a result thereof, electrosurgical energy is transferred from jaw member 2110" through the tissue and to jaw member 2120". The return electrode 2550 remains off or neutral.

In a monopolar mode, jaw member 2110" and 2120" are both energized with the same electrical potential and the return pad 2550 is energized with a second electrical potential forcing the electrical current to travel from the jaw members 2110" and 2120", through the tissue and to the return electrode 2550. This enables the jaw members 2110" and 2120" to treat tissue in a monopolar fashion that, as mentioned above, advantageously treats a vascular tissue structures and/or allows quick dissection of narrow tissue planes. As can be appreciated, all of the leads 2510, 2520 and 2530 may be deactivated when the forceps 2010" is turned off or idle.

Yet again, as discussed previously with respect to FIG. 29, the tubular insulating boot 2500 is included that is configured to mount over the pivot 2103 and at least a portion of the end effector assembly 2100'.

Figure 35A:
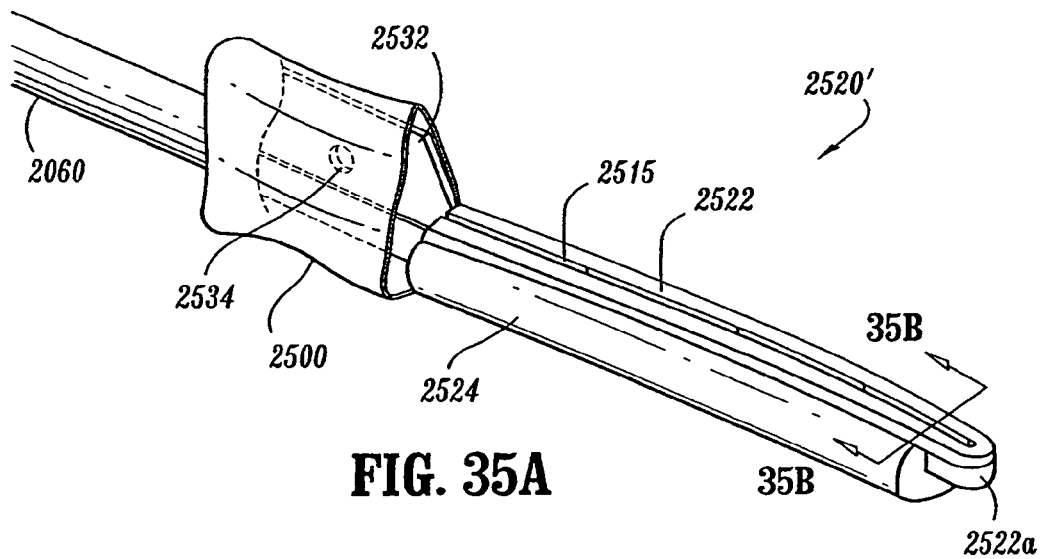
FIGS. 35A and 35B are enlarged views of an alternate embodiment of the second jaw member configured with an insulating boot according to the present disclosure.
Figure 35B:
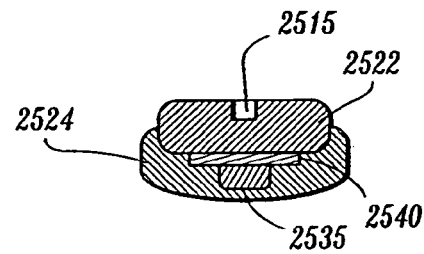

FIGS. 35A and 35B show an alternate embodiment of the forceps 2010 according to the present disclosure that includes a second or bottom jaw member 2520' that is manufactured such that the distal end 2522a of the tissue sealing surface 2522 extends beyond the bottom jaw housing 2524. More particularly, in this particular embodiment, the tissue sealing surface 2522 is made from a stamped sheet metal that is formed atop a stamped sheet metal skeleton 2532. The proximal end of the sheet metal skeleton 2532 may be configured with various pivot points (or apertures 2534), cam slots or grooves depending upon the particular type of pivot action associated with the forceps 2010. As can be appreciated, the sealing surface 2522 may be supported atop a hem or spine 2535 that extends along the skeleton 2532 by many ways known in the art.

An insulating layer 2540 is disposed between the skeleton 2532 and the tissue sealing surface 2522 to isolate the electrically conductive sealing surface 2522' from hem 2535 during activation. The stamped tissue sealing surface 2522' is formed of a double layer of sheet metal material separated by a slot or knife channel 2515 that allows selective reciprocation of a knife, such as knife 2185 disclosed in FIGS. 33A-33C, therein. The distal end 2522a of the tissue sealing surface 2522 may be bent 180° to provide a larger conductive surface area that extends beyond the jaw housing 2524.

It is envisioned that the tissue sealing surface 2522 may be curved or straight depending upon a particular surgical purpose. The jaw housing 2524 may be overmolded to encapsulate the hem 2535 of the skeleton 2532 and sealing plate 2522 that serves to insulate surrounding tissue from the conductive surfaces of the sealing plate 2522 as well as to give the jaw member 2520' a desired shape at assembly.

In a similar manner as discussed previously with respect to FIG. 29, and as shown in FIG. 32, the tubular insulating boot 2500 is included of which one end is configured to mount over the sheet metal skeleton 2532 and pivot pin aperture 2534 and another end of the insulating boot 2500 configured to mount over at least a portion of an exterior surface of reciprocating sleeve 2060. The tubular insulating boot 2500 is flexible to permit opening and closing of the jaw members 2110 and 2520' about pivot 2103.

Details relating to the forceps 2010', which is manufactured such that the distal end 2522a' of the tissue sealing surface 2522 extends beyond the bottom jaw housing 2524, are disclosed in previously mentioned commonly owned U.S. patent application Ser. No. 10/970,307 that is incorporated by reference herein.

Figure 36A:
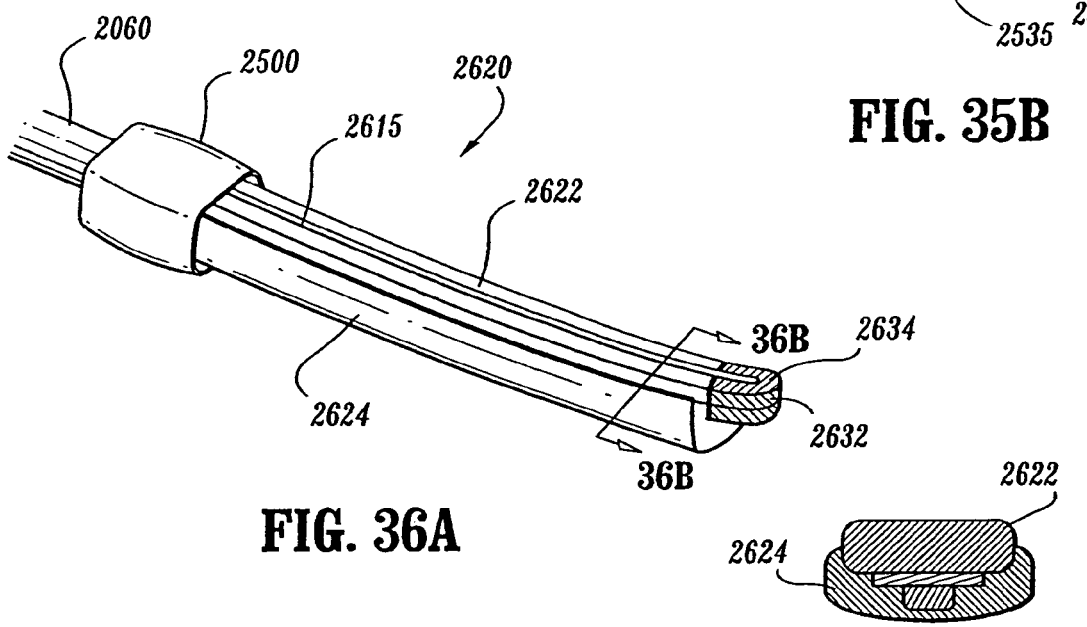
FIGS. 36A and 36B are enlarged views of another alternate embodiment of the second jaw member configured with an insulating boot according to the present disclosure.
Figure 36B:
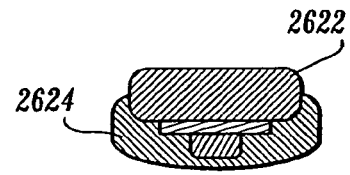

FIGS. 36A and 36B show another embodiment of the bottom or second jaw member 2620 that includes both an electrically conductive sealing surface 2622 for sealing purposes as well as an electrically conductive surface 2632 that is designed for monopolar activation. More particularly, the bottom jaw member 2620 includes a jaw housing 2624 that supports (or encapsulates) a tissue sealing surface 2622. A knife channel 2615 is disposed along the length of the tissue sealing surface 2622 and allows reciprocation of a knife therein. An insulating layer 2634 is positioned at or proximal to the distal end of the tissue sealing surface 2622 distal to the knife channel 2615. A second conductive material 2632 (that may or may not be the same material as tissue sealing surface 2622) is disposed on the opposite side of the insulating layer 2634.

It is envisioned that the insulating material 2634 will isolate the monopolar portion 2632 during electrical activation of tissue surface 2622 and isolate the tissue surface 2622 during electrical activation of monopolar element 2632. As can be appreciated, the two different electrically conductive elements 2622 and 2632 are connected to electrical generator 2300 by different electrical connections and may be selectively activated by the user. Various switches or electrical control elements or the like (not shown) may be employed to accomplish this purpose.

Still yet again, to further enhance safety, as discussed previously with respect to FIG. 29, the tubular insulating boot 2500 is included that is configured to mount over the pivot (not shown) and at least a portion of the end effector assembly. The tubular insulating boot 2500 is flexible to permit opening and closing of the jaw members 2110 and 2620.

Bottom or second jaw member 2620 includes both an electrically conductive sealing surface 2622 for sealing purposes as well as an electrically conductive surface 2632 that is designed for monopolar activation are disclosed in previously mentioned commonly owned U.S. patent application Ser. No. 10/970,307 which is incorporated by reference herein.

Figure 37A:
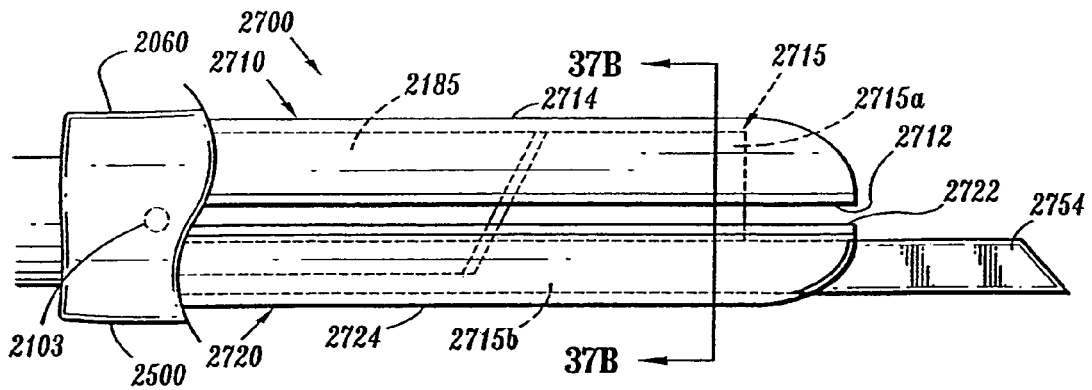
FIGS. 37A and 37B are enlarged views of another alternate embodiment of the end effector assembly configured with an insulating boot according to the present disclosure showing the monopolar element in an extended configuration.
Figure 37B:
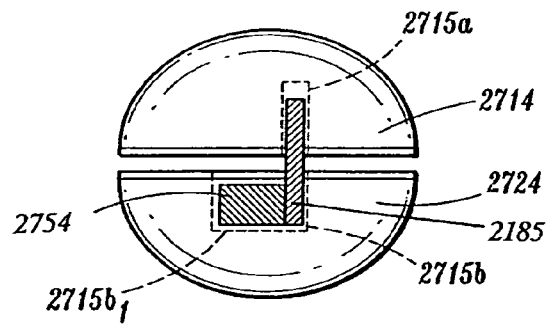

FIGS. 37A and 37B show another embodiment of an end effector assembly 2700 according to the present disclosure that includes top and bottom jaw members 2710 and 2720, respectively each including similar jaw elements as described above, i.e., tissue sealing surfaces 2712 and 2722, respectively and insulative housings 2714 and 2724, respectively. In a similar manner as mentioned above with respect to tissue sealing surface 2622 and knife channel 2615, the tissue sealing surfaces 2712 and 2722 of jaw members 2710 and 2720 mutually cooperate to form a knife channel 2715 that allows knife 2185 to be selectively reciprocated therethrough. More particularly, jaw member 2710 includes a first part of knife channel 2715a and jaw member 2720 includes a second part of the knife channel 2715b that align to form knife channel 2715.

As best shown in FIG. 37B, knife channels 2715a and 2715b are aligned in vertical registration along one side of the jaw members 2710 and 2720 to allow reciprocation of knife 2185 therethrough. Knife channel 2715b of jaw member 2720 is wider (i.e., as measured transversally across the length of the jaw member 2720) and includes a separate channel 2715b1 that is dimensioned to slidingly receive a monopolar element 2754 therethrough. A trigger 70 (or the like) may be utilized as described above with respect to FIGS. 26-31 to extend the monopolar element 2754 for treatment of tissue. In addition, the monopolar element 2754 and the knife 2185 may be made of separate components, as shown, or the monopolar element 2754 and the knife 2185 may be integral with one another.

As can be appreciated various switching algorithms may be employed to activate both the bipolar mode for vessel sealing and the monopolar mode for additional tissue treatments (e.g., dissection). Also, a safety or lockout may be employed either electrically, mechanically or electromechanically to "lock out" one electrical mode during activation of the other electrical mode. In addition, a toggle switch (or the like) may be employed to activate one mode at a time for safety reasons. The monopolar element 2754 may also include a safety (either mechanical, electrical or electro-mechanical—not shown) that only allows electrical activation of the monopolar element 2754 when the monopolar element 2754 is extended from the distal end of jaw member 2720. Insulating boot 2500 is included that is configured to mount over the pivot 2103 and at least a portion of the end effector assembly 2100.

Figure 38A:
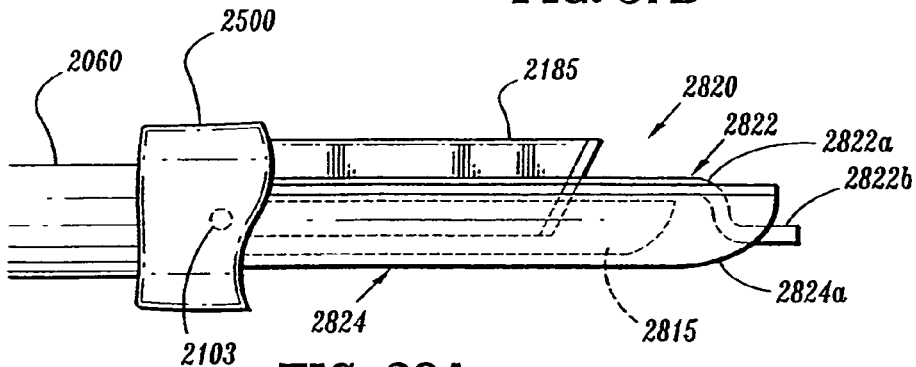
FIGS. 38A and 38B are enlarged views of yet another alternate embodiment of the second jaw member configured with an insulating boot according to the present disclosure.
Figure 38B:
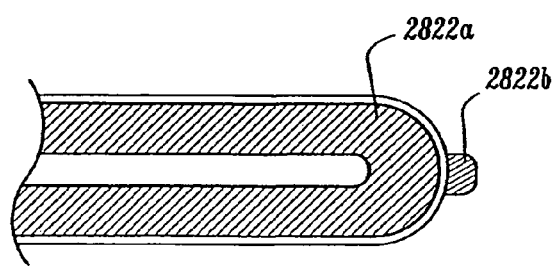

FIGS. 38A and 38B show yet another embodiment of bottom jaw member 2820 that may be utilized for both bipolar vessel sealing and monopolar tissue dissection or other monopolar tissue treatments. More particularly, jaw member 2820 includes an outer jaw housing 2824 that is overmolded to encapsulate a tissue sealing plate 2822 therein. Tissue sealing plate 2822 includes a knife channel 2815 for reciprocating a knife as described in detail above. Tissue sealing plate 2822 also includes a sealing surface 2822a that is disposed in opposing relation to a corresponding sealing surface (not shown) on the opposite upper jaw member (not shown).

Tissue sealing surface 2822 also includes a sealing surface extension 2822b that extends through a distal end 824a of the overmolded jaw housing 2824. As can be appreciated, sealing surface extension 2822b is designed for monopolar tissue dissection, enterotomies or other surgical functions and may be separately electrically energized by the user by a hand switch, footswitch or at the generator 2300 in a similar manner as described above (See FIG. 34B). As can be appreciated, the extension 2822b also serves to further anchor the sealing plate 2822 in the jaw housing 2824 during the overmolding process. Insulating boot 2500 is included that is configured to mount over the pivot 2103 and at least a portion of the end effector assembly.

From the foregoing and with reference to the various figure drawings, those skilled in the art will appreciate that certain modifications can also be made to the present disclosure without departing from the scope of the same. For example and although the general operating components and inter-cooperating relationships among these components have been generally described with respect to a vessel sealing forceps, other instruments may also be utilized that can be configured to allow a surgeon to selectively treat tissue in both a bipolar and monopolar fashion. Such instruments include, for example, bipolar grasping and coagulating instruments, cauterizing instruments, bipolar scissors, etc.

Furthermore, those skilled in the art recognize that while the insulating boots 500, 1500, or 2500 are disclosed as having a generally tubular configuration, the cross-section of the generally tubular configuration can assume substantially any shape such as, but not limited to, an oval, a circle, a square, or a rectangle, and also include irregular shapes necessary to cover at least a portion of the jaw members and the associated elements such as the pivot pins and jaw protrusions, etc.

In addition, while several of the disclosed embodiments show endoscopic forceps that are designed to close in a unilateral fashion, forceps that close in a bilateral fashion may also be utilized with the insulating boot described herein. The presently disclosed insulating boot may be configured to fit atop or encapsulate pivot or hinge members of other known devices such as jawed monopolar devices, standard laparoscopic "Maryland" dissectors and/or bipolar scissors.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An electrosurgical forceps, comprising:

a shaft having a pair of jaw members at a distal end thereof, the jaw members being movable about a pivot from a first position wherein the jaw members are disposed in spaced relation relative to one another to a second position wherein the jaw members are closer to one another for grasping tissue, the shaft defining a longitudinal axis therethrough;

a movable handle that actuates a drive assembly to move the jaw members relative to one another;

at least one of the jaw members including a tissue-engaging surface adapted to connect to a source of electrical energy such that the at least one jaw member is capable of conducting energy to tissue held therebetween; and a flexible insulating boot mounted over the pivot, the flexible insulating boot having a proximal portion disposed on a portion of the shaft and a distal portion disposed on a portion of an exterior surface of the pair of jaw members proximal to the tissue-engaging surface of the at least one jaw member, the proximal portion and the distal portion of the flexible insulating boot disposed such that the flexible insulating boot remains in a substantially stationary position relative to the longitudinal axis and with respect to a reciprocating sleeve of the drive assembly and the jaw members when the drive assembly mechanically advances the reciprocating sleeve to apply a predetermined closure force between the jaw members.

2. An electrosurgical forceps according to claim 1, wherein at least one of the jaw members includes a series of stop members disposed thereon for regulating distance between the jaw members such that a gap is created between the jaw members during the sealing process.

3. An electrosurgical forceps according to claim 1, wherein the forceps includes a knife that is selectively deployable to cut tissue disposed between the jaw members.

4. An electrosurgical forceps according to claim 1, wherein the insulating boot is made of at least one of a viscoelastic, elastomeric, and flexible material suitable for use with a sterilization process that does not substantially impair structural integrity of the boot.

5. An electrosurgical forceps according to claim 4, wherein the sterilization process includes ethylene oxide.

6. An electrosurgical forceps according to claim 1, wherein the flexible insulating boot has a generally tubular configuration.

7. An electrosurgical forceps according to claim 1, wherein two jaw members are adapted to connect to the source of electrical energy such that the jaw members are capable of treating tissue in a bipolar manner upon selective activation of the forceps.

8. An electrosurgical forceps according to claim 1, wherein at least one jaw member is adapted to connect to the source of electrical energy such that the at least one jaw members is capable of treating tissue in a monopolar manner upon selective actuation of the forceps.

* * * * *